(12) United States Patent
Von Haimberger et al.

(10) Patent No.: US 11,103,158 B2
(45) Date of Patent: Aug. 31, 2021

(54) PURE NON-INVASIVE METHOD FOR IDENTIFICATION OF ORGAN DISEASES OR IMPAIRED ORGAN FUNCTION BY INVESTIGATION OF MARKER SUBSTANCES IN EXHALED AIR STIMULATED BY INHALED MARKER SUBSTANCES

(71) Applicants: FREIE UNIVERSITÄT BERLIN, Berlin (DE); Margarete Maria Helene Haimberger, Berlin (DE)

(72) Inventors: Theodore Von Haimberger, Berlin (DE); Anja Heyne, Beelitz-Buchholz (DE); Karsten Heyne, Beelitz-Buchholz (DE)

(73) Assignee: FREIE UNIVERSITÄT BERLIN, Berlin (DE)

( * ) Notice: Subject to any disclaimer, the term of this patent is extended or adjusted under 35 U.S.C. 154(b) by 0 days.

(21) Appl. No.: 15/760,211

(22) PCT Filed: Sep. 14, 2016

(86) PCT No.: PCT/EP2016/071729
§ 371 (c)(1),
(2) Date: Mar. 14, 2018

(87) PCT Pub. No.: WO2017/046183
PCT Pub. Date: Mar. 23, 2017

(65) Prior Publication Data
US 2018/0267016 A1    Sep. 20, 2018

(30) Foreign Application Priority Data
Sep. 14, 2015 (DE) .................... 10 2015 217 511.1
Nov. 6, 2015 (DE) .................... 10 2015 221 862.7

(51) Int. Cl.
| | | |
|---|---|---|
| A61K 49/00 | (2006.01) |
| A61B 5/08 | (2006.01) |
| A61B 5/00 | (2006.01) |
| G01N 33/497 | (2006.01) |
| G16H 50/30 | (2018.01) |
| G16H 50/20 | (2018.01) |
| G01N 33/58 | (2006.01) |
| G16H 10/40 | (2018.01) |
| G16H 20/60 | (2018.01) |

(52) U.S. Cl.
CPC ............ *A61B 5/082* (2013.01); *A61B 5/4244* (2013.01); *G01N 33/497* (2013.01); *G01N 33/58* (2013.01); *G16H 50/20* (2018.01); *G16H 50/30* (2018.01); *G16H 10/40* (2018.01); *G16H 20/60* (2018.01)

(58) Field of Classification Search
None
See application file for complete search history.

(56) References Cited

U.S. PATENT DOCUMENTS

| | | | |
|---|---|---|---|
| 6,221,026 B1 * | 4/2001 | Phillips ................ | G01N 33/497 128/898 |
| 8,920,334 B2 | 12/2014 | Stockmann et al. | |
| 9,541,497 B2 | 1/2017 | Heyne et al. | |
| 2011/0313677 A1 | 12/2011 | Heyne | |
| 2012/0330116 A1 | 12/2012 | Eggers et al. | |
| 2015/0233895 A1 * | 8/2015 | Koo ........................ | C12Q 1/04 514/3.6 |

FOREIGN PATENT DOCUMENTS

| | | |
|---|---|---|
| WO | 2007/000145 A2 | 1/2007 |
| WO | 2009/147576 A2 | 12/2009 |
| WO | 2011/076803 A1 | 6/2011 |
| WO | 2011/076804 A2 | 6/2011 |
| WO | 2012/140213 A2 | 10/2012 |
| WO | 2015/077843 A2 | 10/2012 |
| WO | 2017/046183 A1 | 3/2017 |

OTHER PUBLICATIONS

Probert et al. (J. Gastrointestin Liver Dis 2009, 18, 337-343).*
Liu et al. (Environmental Research 2009, 109, 193-199).*
Alonso, M., and Sanchez, J.M., "Analytical challenges in breath analysis and its application to exposure monitoring", TrAC-Trends in Analytical Chemistry, vol. 44, pp. 78-89 (Mar. 2013).
Aman, A., et al., "Applications of breath gas analysis in medicine", International Journal of Mass Spectrometry, vol. 239, Issues 2-3, pp. 227-233 (Dec. 15, 2004).
Babock, L.M., and Adams, N.G., "Advances in gas phase ion chemistry", Band 4, (University of Georgia). Elsevier Science B.V., All rights reserved: Amsterdam-Nederland, (Dec. 21, 2001).
Badjagbo, K., "Potential of breath analysis: from environmental exposure assessment to medical diagnosis", WebmedCentral Environmental Medicine, Review articles, vol. 3, Issue 3, pp. 1-6 (2012).
Baruque, S.L., et al., "13C-phenylalanine and 13C-methacetin breath test to evaluate functional capacity of hepatocyte in chronic liver disease", Digestive and Liver Disease, vol. 32, Issue 3, pp. 226-232 (2000).
Blom, H.J., and Tangerman, A., "Methanethiol metabolism in whole blood", The Journal of Laboratory and Clinical Medicine, vol. 111, Issue 6, pp. 606-610 (1988).

(Continued)

*Primary Examiner* — Michael G. Hartley
*Assistant Examiner* — Melissa J Perreira
(74) *Attorney, Agent, or Firm* — Maschoff Brennan

(57) ABSTRACT

The disclosure relates to a method for providing original data that can be used for subsequently determining the function of an organ of a living organism or for subsequently diagnosing a disease or a severity of a disease of an organ of a living organism. This method is characterized by several steps, one of which is administering a marker substance to a living organism by inhalation, wherein the marker substance has a vapor pressure above 0.01 mmHg at 37° C. In other method steps, the concentration of this marker substance in exhaled air is determined at at least two different time points. Then, a difference in marker substance concentration is calculated.

7 Claims, 10 Drawing Sheets

(56) References Cited

OTHER PUBLICATIONS

Cao, W., and Duan, Y., "Current status of methods and techniques for breath analysis", Critical Reviews in Analytical Chemistry, vol. 37, Issue 1, pp. 3-13 (Mar. 2, 2007).

Dadamio, J., et al., "Breath biomarkers of liver cirrhosis", Journal of Chromatography. B, Analytical Technologies in the Biomedical and Life Science, vol. 905, pp. 17-22 (Sep. 15, 2012).

Diskin, A.M., et al., "Time variation of ammonia, acetone, isoprene and ethanol in breath: a quantitative SIFT-MS study over 30 days", Physiological Measurement, vol. 24, Issue 1, pp. 107-119 (2003).

Festi, D., et al., "Measurement of hepatic functional mass by means of 13C-methacetin and 13C-phenylalanine breath tests in chronic liver disease: comparison with Child-Pugh score and serum bile acid levels", World Journal of Gastroenterology, vol. 11, Issue 1, pp. 142-148 (2005).

Friedman, L.S., et al., "Liver function tests and the objective evaluation of the patient with liver disease", In: Zakim D., Boyer T.D., editors, Hepatology: A textbook of liver disease, Philadelphia: Saunders:, pp. 1134-1145 (1999).

Graus, M., et al., "High resolution PTR-TOF: quantification and formula confirmation of VOC in real time", Journal of the American Society for Mass Spectrometry, vol. 21, Issue 6, pp. 1037-1044 (Jun. 2010).

Holzhutter, H.G., et al. "Assessment of hepatic detoxification activity: proposal of an improved variant of the (13) C-methacetin breath test", PLoS One, vol. 8, Issue 8, pp. 1-10, e70780 (2013).

Kohl, I., et al. "Smokers breath as seen by Proton-Transfer-Reaction Time-of-Flight Mass Spectrometry (PTR-TOF-MS)", Volatile Biomarkers Non-Invasive Diagnosis in Physiology and Medicine, edited by Amann A. and Smith D., pp. 89-116 (2013).

Inomata, S., et al., "PTR-MS measurements of non-methane volatile organic compounds during an intensive field campaign at the summit of Mount Tai, China, in Jun. 2006", Atmospheric Chemistry and Physics, vol. 10, pp. 7085-7099 (2010).

Gouw, J.DE. and Warneke, C. , "Measurements of volatile organic compounds in the earth's atmosphere using proton-transfer-reaction mass spectrometry", Mass Spectrometry Reviews, vol. 26, Issue 2, pp. 223-257 (2007).

Jan, B., et al., "Computational methods for metabolomic data analysis of ion mobility spectrometry data-reviewing the state of the art", Metabolites, review article, vol. 2, Issue 4, pp. 733-755 (2012).

Jardine, K.J., et al., "Dynamic solution injection: a new method for preparing pptv-ppbv standard atmospheres of volatile organic compounds", Atmospheric Measurement Techniques, vol. 3, pp. 1569-1576 (2010).

Johnson, P.J., "Role of the standard 'liver function tests' in current clinical practice", Annals of Clinical Biochemistry, vol. 26, Pt. 6, pp. 463-471 (Nov. 1989).

Keck, L., et al., "Effects of carbon dioxide in breath gas on proton transfer reaction-mass spectrometry (PTR-MS) measurements", International Journal of Mass Spectrometry, vol. 270, Issue 3, pp. 156-165 (2008).

Khero, S., et al., "Co-relation of high serum ammonia levels with severity of hepatic encephalopathy in chronic liver disease patients", Rawal Medical Journal, vol. 39, Issue 2, pp. 119-123 (2014).

King, J., et al., "Physiological modeling for analysis of exhaled breath", in: "Volatile Biomarkers-Non-Invasive Diagnosis in Physiology and Medicine", A. Amann and D. Smith (eds), Elsevier, pp. 27-46 (2013).

Kushch, I., et al. "Compounds enhanced in a mass spectrometric profile of smokers' exhaled breath versus non-smokers as determined in a pilot study using PTR-MS", Journal of Breath Research, vol. 2, Issue 2, pp. 1-26, 026002 (2008).

Kwak, J., et al., "Evaluation of bio-VOC sampler for analysis of volatile organic compounds in exhaled breath", Metabolites, vol. 4, Issue 4, pp. 879-888 (2014).

Lindinger, W., et al., "Endogenous production of methanol after the consumption of fruit", Alcoholism Clinical and Experimental Research, vol. 21, Issue 5, pp. 939-943 (Aug. 1997).

Lindinger, W. and Jordan, A., "Proton-transfer-reaction mass spectrometry (PTR-MS): on-line monitoring of volatile organic compounds at pptv levels", Chemical Society Reviews, vol. 27, pp. 347-354 (1998).

Lock, J.F., "Interpretation of non-invasive breath tests using (13)C-labeled substrates—a preliminary report with (13) C-methacetin", European Journal of Medical Research, vol. 14, Issue 12, pp. 547-550 (2009).

Maddula, S., et al., "Correlation analysis on data sets to detect infectious agents in the airways by ion mobility spectrometry of exhaled breath", International Journal for Ion Mobility Spectrometry, vol. 14, Issue 4, pp. 197-206 (2011).

Mathews, T.L., et al., "Technologies for clinical diagnosis using expired human breath analysis", Review Article, Diagnostics, vol. 5, Issue 1, pp. 27-60 (2015).

Mathews, J.M., et al., "Do endogenous volatile organic chemicals measured in breath reflect and maintain CYP2E1 levels in vivo?", Toxicology and Applioed Pharmacology, vol. 146, Issue 2, pp. 255-260 (1997).

Matsumoto, K., et al., "[13C]methacetin breath test for evaluation of liver damage", Digestive Disease and Science, vol. 32, Issue 4, pp. 344-348 (1987).

Michael, N.G., "Cancer Chemoprevention and Therapy by Monoterpenes", Environmental Health Perspectives, vol. 105, Supplement 4, pp. 977-979 (1997).

Miekisch, W., et al., "Diagnostic potential of breath analysis-focus on volatile organic compounds", Clinica Chimica Acta., vol. 347, Issues 1-2, pp. 25-39 (2004).

Miyazawa, M. et al., "Metabolism of (+ )- and (−)-Limonenes to respective carveols and perillyl alcohols by CYP2C9 and CYP2C19 in Human Liver Microsomes." Drug Metabolism and Disposition, vol. 30, Issue 5, 602-607 (2002).

Mochalski, P., et al. "Blood and breath levels of selected volatile organic compounds in healthy volunteers", Analyst., vol. 138, Issue 7, pp. 2134-2145 (2013).

Modak, A.S., "An update on 13C-Breath Tests: The transition to acceptability into clinical practice", Volatile Biomarkers: Non-Invasive Diagnosis in Physiology and Medicine', edited by A. Amann and D. Smith, Chapter 14, pp. 245-262 (2013).

Modak, A.S., "Regulatory Issues on breath tests and updates of recent advances on [13C]-breath tests", Journal of Breath Research, vol. 7, Issue 3, pp. 1-8, 037103 (2013).

Nastainczyk, W., et al., "The reductive metabolism of halogenated alkanes by liver microsomal cytochrome P450", Biochemical Pharmacology, vol. 31, Issue 3, pp. 391-396 (1982).

Vavarro-Alarcon, M., et al., "Selenium concentrations in serum of individuals with liver diseases (cirrhosis or hepatitis): relationship with some nutritional and biochemical markers", The Science of Total Envoirment, vol. 291, Issue 1-3, pp. 135-141 (2002).

Pauling, L., et al., "Quantitative analysis of urine vapor and breath by gas-liquid partition chromatography", Proceedings of the National Academy of Sciences of the United States of America, vol. 68, Issue 10, pp. 2374-2376 (1971).

Petrolati, A., et al., "13C-methacetin breath test for monitoring hepatic function in cirrhotic patients before and after liver transplantation", Alimentary Pharmacology & Therapeutics, vol. 18, Issue 8, pp. 785-790 (2003).

Phillips, M., et al., "Metabolic and environmental origins of volatile organic compounds in breath", Journal of Clinical Pathology, vol. 47, Issue 11, pp. 1052-1053 (1994).

Phillips, M., et al., "Variation in volatile organic compounds in the breath of normal humans", Journal of Chromatography B: Biomedical Sciences and Applications, vol. 729, Issues 1-2, pp. 75-88 (1999).

Pobert, C.S., et al., "Volatile organic compounds as diagnostic biomarkers in gastrointestinal and liver diseases", J. Gastrointestin. Liver Dis., Review, vol. 18, Issue 3, pp. 337-343 (2009).

Riecke, B., et al., "Major influence of oxygen supply on 13CO2:12CO2 ratio measurement by nondispersive isotope-selective infrared spectroscopy", Helicobacter., vol. 10, Issue 6, pp. 620-622 (2005).

Rieder, J., et al., "Analysis of volatile organic compounds: possible applications in metabolic disorders and cancer screening", Wien. Klin. Wochenschr., vol. 113, Issues 5-6, pp. 181-185 (2001).

(56) References Cited

OTHER PUBLICATIONS

Rieders, F., "Noxious gases and vapors. I: Carbon monoxide, cyanides, methemoglobin, and sulfhemoglobin", In: DePalma JR, ed. Drill's pharmacology in medicine, 4th ed. New York, NY, McGraw-Hill Book Company, pp. 1180-1205 (1971).
Ropcke, J., and Hannemann, M., "Special section on breath gas analysis", Journal of Breath Research, vol. 5, Issue 2, pp. 1-2, 020201 (2011).
Rubin, T., et al., "Quantitative determination of metabolization dynamics by a real-time 13CO2 breath test", Journal of Breath Research, vol. 5, Issue 2, pp. 1-6, 027102 (2011).
S. Van den Velde et al., "GC-MS analysis of breath odor compounds in liver patients", Journal of Chromatography B. Analytical Technologies in the Biomedical and Life Sciences, vol. 875, Issue 2, pp. 344-348 (2008).
Schoeller, D.A., et al., "Clinical diagnosis with the stable isotope 13C in CO2 breath tests: methodology and fundamental considerations", Journal of Laboratory and Clinical Medicine, vol. 90, Issue 3, pp. 412-421 (1977).
Scymczak, W., et al., "Breath gas analysis in unrestrained mice: A survey of VOC screening using PTR-TOF 2000", Applications in Medicine and Biotechnology, 6th International Conference on Proton Transfer Reaction Mass Spectrometry and its Applications, A. Hansel and J. Dunkl Contributions, Institut für Ionenphysik und Angewandte Physik, Universität Innsbruck, innsbruck university press, 1st edition, pp. 40 (2013),http://www.uibk.ac.at/iup/buch_pdfs/ptrms_2013.pdf.
Shaji, J., and Jadhav, D., "Breath biomarker for clinical diagnosis and different analysis technique", Research Journal of Pharmaceutical, Biological and Chemical Sciences, India, vol. 1, Issue 3, pp. 639-653 (2010).
Smith, D., et al., "On-line, simultaneous quantification of ethanol, some metabolites and water vapour in breath following the ingestion of alcohol", Physiol. Meas., vol. 23, Issue 3, pp. 477-489 (2002).
Smith. D., et al., "Trace gases in breath of healthy volunteers when fasting and after a protein-calorie meal: a preliminary study", Journal of Applied Physiology, vol. 87, Issue 5, pp. 1584-1588 (1999).
Spanel, P., and Smith, D., "Influence of weakly bound adduct ions on breath trace gas analysis by selected ion flow tube mass spectrometry (SIFT-MS)", International Journal of Mass Spectrometry, vol. 280, Issue 1-3, pp. 128-135 (2009).
Spanel, P., et al., "The concentration distributions of some metabolites in the exhaled breath of young adults", Journal of Breath Research, vol. 1, Issue 2, pp. 1-8, 026001 (2007).
Stephan, A., et al., "Novel analytical tools for food flavour", Food Research International, vol. 33, Issues 3-4, pp. 199-209 (2000).
Stockmann, M., "Wertigkeit eines neu entwickelten Verfahrens zur Bestimmung der Leberfunktion in der Leberchirurgie (LiMAx-Test)", Habilitationsschrift, zur Erlangung der Lehrbefähigung für das Fach Chirurgie, vorgelegt dem Fakultätsrat der Medizinischen Fakultät Charité—Universitätsmedizin Berlin (2009).
Stockmann, M., et al., "Prediction of postoperative outcome after hepatectomy with a new bedside test for maximal liver function capacity", Annals of Surgery, vol. 250, Issue 1, pp. 119-125 (2009).
Stockmann, M., et al., "The LiMAx test: a new liver function test for predicting postoperative outcome in liver surgery", HPB (Oxford), vol. 12, Issue 2, pp. 139-146 (2010).
Suha, Al-Ani. "Analysis of breath allows for non-invasive identification and quantification of diseases and metabolic dysfunction." www.diss.fu-berlin.de/diss/receive/FUDISS_thesis_000000100227.
Tangerman, A., et al., "Cause and composition of foetor hepaticus", Lancet, vol. 343, Issue 8895, pp. 483 (1994).
Thekedar, B., "Investigations on the use of breath gas analysis with Proton Transfer Reaction Mass Spectrometry (PTR-MS) for a non-invasive method of early lung cancer detection", Technische Universität München, Fakultät für Physik, Ph.D. Diss. (2009), https://mediatum.ub.tum.de/doc/821780/821780.pdf.
Thekedar, B., et al., "Investigations of the variability of breath gas sampling using PTR-MS", Journal of Breath Research, vol. 3, Issue 2, pp. 1-11, 027007 (2009).
Turner, C., et al., "A longitudinal study of ammonia, acetone and propanol in the exhaled breath of 30 subjects using selected ion flow tube mass spectrometry, SIFT-MS", Physiological Measurement, vol. 27, Issue 4, pp. 321-337 (2006).
Tygstrup, N., et al., "Assessment of liver function: principles and practice", Journal of Gastroenterology and Hepatology, vol. 5, Issue 4, pp. 468-482 (1990).
Wallace, L., et al., "Exposures to benzene and other volatile organic compounds from active and passive smoking", Archives of Environmental Health, vol. 42, Issue 5, pp. 272-279 (1987).
Wang, C. and Sahay, P., "Breath analysis using laser spectroscopic techniques: breath biomarkers, spectral fingerprints, and detection limits", Review Article, Sensors, vol. 9, Issue 10, pp. 8230-8262 (2009).
Wehinger, A., et al, "Lung cancer detection by proton transfer reaction mass-spectrometric analysis of human breath gas", International Journal of Mass Spectrometry, vol. 265, Issue 1, pp. 49-59 (2007).
Bednarsch, J. et al., "Noninvasive diagnosis of chemotherapy induced liver injury by LiMAx test—two case reports and a review of the literature," BMC Research Notes, pp. 1-5 (2015).
Brinkhaus, G., et al., "CT-Guided High-Dose-Rate Brachytherapy of Liver Tumours Does Not Impair Hepatic Function and Shows High Overall Safety and Favourable Survival Rates" Ann Surg Oncol, vol. 21, pp. 4284-4292 (2014).
Docke, S., et al., "Elevated hepatic chemerin gene expression in progressed human non-alcoholic fatty liver disease," Eur J Endocrinol, vol. 169, pp. 547-557 (2013).
Faber, W., et al., "Implication of Microscopic and Macroscopic Vascular Invasion for Liver Resection in Patients with Hepatocellular Carcinoma," Digestive surgery, vol. 31, No. 3, pp. 204-209 (Sep. 2014).
Faber, W., et al., "Long-term results of liver resection for hepatocellular carcinoma in noncirrhotic liver," Surgery, vol. 153, pp. 510-517 (2013).
Faber, W., et al., "Patient age and extent of liver resection influence outcome of liver resection for hepatocellular carcinoma in non-cirrhotic liver," Hepatogastroenterology, pp. 1-2 (Oct. 2014).
Faber, W., et al., "Significant impact of patient age on outcome after liver resection for HCC in cirrhosis" Eur J Surg Oncol, vol. 40 , pp. 208-213 (2014).
Gebhardt, S., et al., "Risk Factors of Metabolic Disorders After Liver Transplantation: An Analysis of Data From Fasted Patients," Transplantation, vol. 99, pp. 1243-1249 (Jun. 2015).
Geisel, D., et al., "Imaging-based evaluation of liver function: comparison of $^{99}$mTc-mebrofenin hepatobiliary scintigraphy and Gd-EOB-DTPA-enhanced MRI," Springer Berlin Heidelberg, vol. 25, Issue 5, pp. 1384-1391 (Dec. 2, 2014).
Geisel, D., et al., "Improved Hypertrophy of Future Remnant Liver after Portal Vein Embolization with Plugs, Coils and Particles," Cardiovasc Intervent Radiol, vol. 37, pp. 1251-1258 (2014).
Geisel, D., et al., "Increase in left liver lobe function after preoperative right portal vein embolisation assessed with gadolinium-EOB-DTPA MRI," Eur Radiol. vol. 23, pp. 2555-2560 (2013).
Geisel, D., et al., "Evaluation of gadolinium-EOB-DTPA uptake after portal vein embolization: Value of an increased flip angle," Acta Radiol, vol. 55, pp. 149-154 (Mar. 1, 2014).
Holzhutter, H-G., et al., "Assessment of hepatic detoxification activity: proposal of an improved variant of the (13) c-methacetin breath test," PLoS One, vol. 8, No. 8, pp. 1-10 (Aug. 15, 2013).
Hoppe, S., et al., "Nonalcoholic steatohepatits and liver steatosis modify partial hepatectomy recovery," Journal of Investigative Surgery, pp. 24-31 (Nov. 13, 2014).
Jara, M., et al., "Bovine pericardium for portal vein reconstruction in abdominal surgery: a surgical guide and first experiences in a single center," Dig Surg, vol. 32, pp. 135-141 (2015).
Jara, M., et al., "Enhancing safety in liver surgery using a new diagnostic tool for evaluation ofactual liver function capacity" The LiMAx test; Dtsch Med Wochenschr, vol. 139, pp. 387-391 (2014).

(56) References Cited

OTHER PUBLICATIONS

Jara, M., et al., "Predictors of quality of life in patients evaluated for liver transplantation," Clin Transplant, vol. 28, pp. 1331-1338 (2014).

Jara, M., et al., "Reductions in post-hepatectomy liver failure and related mortality after implementation of the LiMAx algorithm in preoperative work-up: a single-centre analysis of 1170 hepatectomies of one or more segments," HPB (Oxford), vol. 17, Issue 7, pp. 651-658 (Jul. 2015).

Kaffarink, M F., et al., "Early diagnosis of sepsis-related hepatic dysfunction and its prognostic impact on survival: A prospective study with the LiMAx test," Critical Care, vol. 17, No. 5, pp. 1-11 (2013).

Kiefer, S., et al., "A novel personal health system with integrated decision support and guidance for the management of chronic liver disease," Stud Health Technol Inform, vol. 205, pp. 83-87 (2014).

Lederer, A., et al., "Postoperative bile leakage inhibits liver regeneration after 70% hepatectomy in rats," J Invest Surg. vol. 26, pp. 36-45 (2013).

Lock, JF., et al., "Predicting the prognosis in acute liver failure: results from a retrospective pilot study using the LiMAx test," Ann Hepatol, vol. 12, pp. 388-394 (2013).

Malinowski, M., et al., "Enzymatic Liver Function Capacity Correlates with Disease Severity of Patients with Liver Cirrhosis: A Study with the LiMAx Test," Dig Dis Sci., vol. 59, pp. 2983-2991 (2014).

Malinowski, M., et al., "Factors influencing hypertrophy of the left lateral liver lobe after portal vein embolization," Langenbeck's Archives of Surgery, vol. 400, Issue 2, pp. 237-246 (Feb. 2015).

Malinowski, M., et al., "Portal vein embolization with plug/coils improves hepatectomy outcome," Journal of surgical research, vol. 194(1), pp. 202-211.

Maximilian, J., et al., "Prognostic value of enzymatic liver function for the estimation of short-term survival of liver transplant candidates: a prospective study with the LiMAx test," Transplant International, vol. 28, No. 1, pp. 52-58 (Jan. 2015).

Maximilian, J., et al., "Reliable assessment of liver function using LiMAx," Journal of Surgical Research vol. 193, pp. 1-2 (Jan. 2015).

"New breath test shows possible biomarker for early-stage liver disease diagnosis," University of Birmingham, Published Aug. 11, 2015.

Strucker, B., et al., "Intraoperative Placement of External Biliary Drains for Prevention and Treatment of Bile Leaks After Extended Liver Resection Without Bilioenteric Anastomosis," World J Surg, vol. 37, pp. 2629-2634 (2013).

Stockmann, M., et al., "How Far Is the Development of 13C-Liver-Function Breath Tests? Dig Dis Sci" vol. 58, pp. 18044-1805 (2013).

\* cited by examiner

PURE NON-INVASIVE METHOD FOR IDENTIFICATION OF ORGAN DISEASES OR IMPAIRED ORGAN FUNCTION BY INVESTIGATION OF MARKER SUBSTANCES IN EXHALED AIR STIMULATED BY INHALED MARKER SUBSTANCES

CROSS-REFERENCE TO A RELATED APPLICATION

This application is a national phase patent application of International patent application PCT/EP 2016/071729, filed on Sep. 14, 2016, which claims priority of German patent application 10 2015 217 511.1, filed on Sep. 14, 2015 and of German patent application 10 2015 221 862.7, filed on Nov. 6, 2015.

BACKGROUND

Aspects of the invention relate to a method for providing original data that can be used for subsequently determining the function of an organ of a living organism or for subsequently diagnosing a disease or a severity of a disease of an organ of a living organism, to the use of specific substances in such a method as well as to the further medical use of such substances in a diagnostic method.

Non-invasive determination of organ diseases, such as liver diseases, or impaired organ function, such as impaired liver function, is an important field of medicine and hepatology. The liver is the organ where most catalytic processes, metabolic reactions, and decomposition of toxic marker substances take place. Thus, the actual metabolic power and overall status of the liver is a crucial information for physicians treating a patient.

Over the last years several new methods were developed to measure the liver function and to identify liver diseases or impaired liver functions. The two most important methods for identification of the liver function are the so-called LiMAx test and the ICG (indiocyano green) test. Both tests are based on a marker substance administered to the patients. The LiMAx-test tracks the metabolization of the $^{13}$C-labelled substrate methacetin as marker substance by detecting the metabolic product $^{13}CO_2$, while the ICG test simply detects the clearing of ICG via the liver and kidney (cf. US 2012/0330116 A1).

The information on the liver status is limited for the ICG test, since the function of the kidney influences the clearing dynamics, and more important the slow clearing dynamics also depend on redistribution processes of ICG within the body, altering the time constant measured. Thus, the ICG test is not able to provide precise information on the liver status.

In contrast, the fast LiMAx test tracks the metabolic product of $^{13}$C-methacetin in real time, gaining information on the liver metabolic dynamics not influenced by redistribution processes within the body. However, the LiMAx test could be influenced by lung function in case of patients with altered lung function or severe lung diseases.

For both tests intravenous administration of the marker substance (ICG or methacetin) is optimal, and oral or intestinal administration is possible. According to current knowledge, none of these tests allows an administration of the marker substance by inhalation. One reason is the necessary high concentration of the marker substance that cannot be achieved by inhalation in case of ICG or methacetin. In addition, neither methacetin nor ICG have a measurable vapor pressure, making a direct inhalation of these substances impossible.

The LiMAx test induces metabolization of $^{13}$C-methacetin and thus belongs to methods using induced metabolization processes after administering a marker substance by tracking a part of the metabolization process. In case of the LiMAx test, a metabolization product is tracked to follow metabolization dynamics. This is exemplarily described in WO 2007/000145 A2, WO 2011/076803 A1, and WO 2011/076804 A2. Some further references relating to scientific literature about the LiMAx test and related liver diseases are given below:

1. Jara M, Reese T, Malinowski M, Valle E, Seehofer D, Puhl G, Neuhaus P, Pratschke J, Stockmann M; *Reductions in post-hepatectomy liver failure and related mortality after implementation of the LiMAx algorithm in preoperative work-up: a single—centre analysis of 1170 hepatectomies of one or more segments*; HPB (Oxford). 2015; 17:651-8.
2. Bednarsch J, Jara M, Lock J F, Malinowski M, Pratschke J, Stockmann M.; *Noninvasive diagnosis of chemotherapy induced liver injury by LiMAx test—two case reports and a review of the literature*; BMC Res Notes. 2015; 8:99
3. Malinowski M, Stary V, Lock J F, Schulz A, Jara M, Seehofer D, Gebauer B, Denecke T, Geisel D, Neuhaus P, Stockmann M.; *Factors influencing hypertrophy of the left lateral liver lobe after portal vein embolization*; Langenbecks Arch Surg. 2015; 400:237-46.
4. Jara M, Malinowski M, Bahra M, Stockmannn M, Schulz A, Pratschke J, Puhl G.; *Bovine pericardium for portal vein reconstruction in abdominal surgery: a surgical guide and first experiences in a single center*; Dig Surg. 2015; 32:135-41.
5. Gebhardt S, Jara M, Malinowski M, Seehofer D, Puhl G, Pratschke J, Stockmann M.; *Risk Factors of Metabolic Disorders After Liver Transplantation: An Analysis of Data From Fasted Patients*; Transplantation. 2015; 99:1243-9.
6. Malinowski M, Geisel D, Stary V, Denecke T, Seehofer D, Jara M, Baron A, Pratschke J, Gebauer B, Stockmann M.; *Portal vein embolization with plug/coils improves hepatectomy outcome*; J Surg Res. 2015; 194:202-11.
7. Geisel D, Lüdemann L, Fröling V, Malinowski M, Stockmann M, Baron A, Gebauer B, Seehofer D, Prasad V, Denecke T.; *Imaging-based evaluation of liver function: comparison of 99mTc-mebrofenin hepatobiliary scintigraphy and Gd-EOB-DTPA-enhanced MRI*; Eur Radiol. 2015; 25:1384-91.
8. Hoppe S, von Loeffelholz C, Lock J F, Doecke S, Sinn B V, Rieger A, Malinowski M, Pfeiffer A F, Neuhaus P, Stockmann M.; *Nonalcoholic Steatohepatits and Liver Steatosis Modify Partial Hepatectomy Recovery*; J Invest Surg. 2015; 28:24-31.
9. Jara M, Malinowski M, Lüttgert K, Schott E, Neuhaus P, Stockmann M.; *Prognostic value of enzymatic liver function for the estimation of short-term survival of liver transplant candidates: a prospective study with the LiMAx test*; Transpl Int. 2015; 28:52-8.
10. Jara M, Bednarsch J, Valle E, Lock J F, Malinowski M, Schulz A, Seehofer D, Jung T, Stockmann M.; *Reliable assessment of liver function using LiMAx*; J Surg Res. 2015; 193:184-9.
11. Faber W, Sharafi S, Stockmann M, Dennecke T, Bahra M, Klein F, Malinowski M B, Schott E, Neuhaus P, Seehofer D.; *Patient age and extent of liver resection* influence outcome of liver resection for hepatocellular carcinoma in non-cirrhotic liver; Hepatogastroenterology. 2014; 61:1925-30.
12. Faber W, Stockmann M, Kruschke J E, Denecke T, Bahra M, Seehofer D.; *Implication of microscopic and macroscopic vascular invasion for liver resection in patients with hepatocellular carcinoma*; Dig Surg. 2014; 31:204-9.
13. Kiefer S, Schafer M, Bransch M, Brimmers P, Bartolomé D, Baños J, Orr J, Jones D, Jara M, Stockmann M.; *A novel personal health system with integrated decision support and guidance for the management of chronic liver disease*; Stud Health Technol Inform. 2014; 205:83-7.
14. Jara M, Bednarsch J, Malinowski M, Lüttgert K, Orr J, Puhl G, Seehofer D, Neuhaus P, Stockmann M.; *Predictors of quality of life in patients evaluated for liver transplantation*; Clin Transplant. 2014; 28:1331-8.
15. Malinowski M, Jara M, Lüttgert K, Orr J, Lock J F, Schott E, Stockmann M.; *Enzymatic Liver Function Capacity Correlates with Disease Severity of Patients with Liver Cirrhosis: A Study with the LiMAx Test*; Dig Dis Sci. 2014; 59:2983-91.
16. Brinkhaus G, Lock J F, Malinowski M, Denecke T, Neuhaus P, Hamm B, Gebauer B, Stockmann M.; *CT-Guided High-Dose-Rate Brachytherapy of Liver Tumours Does Not Impair Hepatic Function and Shows High Overall Safety and Favourable Survival Rates*; Ann Surg Oncol. 2014; 21:4284-92.
17. Jara M, Bednarsch J, Lock J F, Malinowski M, Schulz A, Seehofer D, Stockmann M.; *Enhancing safety in liver surgery using a new diagnostic tool for evaluation of actual liver function capacity—The LiMAx test*; Dtsch Med Wochenschr. 2014; 139:387-91.
18. Faber W, Stockmann M, Schirmer C, Möllerarnd A, Denecke T, Bahra M, Klein F, Schott E, Neuhaus P, Seehofer D.; *Significant impact of patient age on outcome after liver resection for HCC in cirrhosis*; Eur J Surg Oncol. 2014; 40:208-13.
19. Geisel D, Malinowski M, Powerski M J, Wüstefeld J, Heller V, Denecke T, Stockmann M, Gebauer B.; *Improved Hypertrophy of Future Remnant Liver after Portal Vein Embolization with Plugs, Coils and Particles*; Cardiovasc Intervent Radiol. 2014; 37:1251-8.
20. Kaffarnik M F, Lock J F, Vetter H, Ahmadi N, Lojewski C, Malinowski M, Neuhaus P, Stockmann M.; *Early diagnosis of sepsis-related hepatic dysfunction and its prognostic impact on survival: a prospective study with the LiMAx test*; Crit Care. 2013; 17:R259.
21. Holzhütter H G, Lock J F, Taheri P, Bulik S, Goede A, Stockmann M.; *Assessment of hepatic detoxification activity: proposal of an improved variant of the* (13)*c-methacetin breath test*; PLoS One. 2013; 8:e70780.
22. Döcke S, Lock J F, Birkenfeld A L, Hoppe S, Lieske S, Rieger A, Raschzok N, Sauer I M, Florian S, Osterhoff M A, Heller R, Herrmann K, Lindenmüller S, Horn P, Bauer M, Weickert M O, Neuhaus P, Stockmann M, Möhlig M, Pfeiffer A F, von Loeffelholz C.; *Elevated hepatic chemerin gene expression in progressed human non-alcoholic fatty liver disease*; Eur J Endocrinol. 2013; 169:547-57.
23. Geisel D, Lüdemann L, Wagner C, Stelter L, Grieser C, Malinowski M, Stockmann M, Seehofer D, Hamm B, Gebauer B, Denecke T.; *Evaluation of gadolinium-EOB-DTPA uptake after portal vein embolization: value of an increased flip angle*; Acta Radiol. 2014; 55:149-54.
24. Strücker B, Stockmann M, Denecke T, Neuhaus P, Seehofer D.; *Intraoperative Placement of External Biliary Drains for Prevention and Treatment of Bile Leaks After Extended Liver Resection Without Bilioenteric Anastomosis*; World J Surg. 2013; 37:2629-34.
25. Lock J F, Kotobi A N, Malinowski M, Schulz A, Jara M, Neuhaus P, Stockmann M.; *Predicting the prognosis in acute liver failure: results from a retrospective pilot study using the LiMAx test*; Ann Hepatol. 2013; 12:556-62.
26. Geisel D, Lüdemann L, Keuchel T, Malinowski M, Seehofer D, Stockmann M, Hamm B, Gebauer B, Denecke T.; *Increase in left liver lobe function after preoperative right portal vein embolisation assessed with gadolinium-EOB-DTPA MRI*; Eur Radiol. 2013; 23:2555-60.35. Stockmann M, Lock J F; *How Far Is the Development of* 13C-*Liver-Function Breath Tests?* Dig Dis Sci. 2013; 58:1804-5.
27. Lederer A, It Seehofer D, Schirmeier A, Levasseur S, Stockmann M, Nüssler A K, Menger M D, Neuhaus P, Rayes N.; *Postoperative bile leakage inhibits liver regeneration after 70% hepatectomy in rats*; J Invest Surg. 2013; 26:36-45.
28. Faber W, It Sharafi S, Stockmann M, Denecke T, Sinn B, Puhl G, Bahra M, Malinowski M B, Neuhaus P, Seehofer D.; *Long-term results of liver resection for hepatocellular carcinoma in noncirrhotic liver*; Surgery. 2013; 153:510-7.

WO 2012/140213 A2 describes a method in which a marker substance is administrated, wherein the metabolization products are detected in real time.

SUMMARY

It is an object of the present invention to provide a method that can be used in organ function diagnostics or in (quantitative) diagnostics of organ diseases, wherein the method allows for totally non-invasive administration of a marker substance to a living organism.

It was surprisingly found that inhalation of a marker substance is a suited way of administration, if not a metabolization product of the marker substance, but the marker substance itself is detected afterwards in air exhaled by the living organism. Specifically, a reduction of the concentration of the marker substance in the exhaled air can be directly linked to a metabolization of a part of the marker substance by the living organism in a specific organ. Thereby, the kind of marker substance is the decisive factor for the organ, the function of which is to be determined.

Specifically, the object is solved by a method for providing original data that can be used for subsequently determining the function of an organ of a living organism or for subsequently diagnosing a disease or a severity of a disease of an organ of a living organism. This method is characterized by the following steps:

a) administering a marker substance to a living organism by inhalation, wherein the marker substance has a vapor pressure above 0.01 mmHg at 37° C.,
b) determining a concentration of the marker substance in exhaled air which is exhaled by the living organism at a first time point,
c) determining the concentration of the marker substance in the exhaled air which is exhaled by the living organism at a second time point after the first time point,
d) determining a difference between the concentration of the marker substance determined at the first time point and the concentration of the marker substance determined at the second time point.

The living organism can be, e.g., a rodent or a mammal, such as a human.

Inhalation is a highly non-invasive method to administer a marker substance and guarantees that the lung condition of the living organism is reflected in the uptake/inhalation and release/exhalation of the marker substance.

The method steps can be performed in the sequence indicated above or in any other sequence. If the method steps are performed in the sequence indicated above, the first time point is a time point after inhalation of the marker substance. E.g., it can be a time point directly after inhalation of the marker substance. In this circumstance, "directly" means within less than 1 minute, in particular less than 45 seconds, in particular less than 30 seconds, in particular less than 15 seconds after the end of inhalation of the marker substance.

Such a method step sequence is particularly suited for providing original data to be used in liver function diagnostics or in diagnosing liver diseases.

The second time point is always after the first time point. The time difference between the first time point and the second time point can be, e.g., between from 30 seconds to 2 days. At least two measurements have to be taken, but increasing the number of data points (measurements) increases the certainty of the metabolization dynamics observed indirectly by a decrease of the concentration of the marker substance in the exhaled air.

Suitable time points for a measurement (and therewith also suited differences between the first time point and the second time point) are 30 seconds, 1 minute, 2 minutes, 3 minutes, 5 minutes, 7 minutes, 10 minutes, 20 minutes, 30 minutes, 40 minutes, 50 minutes, 70 minutes, 100 minutes, 200 minutes, 300 minutes, 400 minutes, 500 minutes, 700 minutes, 1000 minutes, 2000 minutes, or 2800 minutes after beginning of inhalation, before the inhalation, or after the end of inhalation.

Information on the metabolization dynamics of the marker substance can be generally gathered from measurements before inhaling the enriched air, while inhaling the enriched air, directly after inhaling the enriched air, and after inhalation of the enriched air at different time points.

In an embodiment, step a) is performed between steps b) and c). Thus, in this embodiment, the first measurement (at the first time point) takes place before the marker substance is inhaled. This means that the first measurement reflects the situation of the living organism before inhalation of the marker substance. Afterwards, the marker substance is inhaled. Then, the concentration of the marker substance is again determined (at the second time point) so that afterwards the difference between the marker substance concentration before inhalation and after inhalation can be calculated. Such a method step sequence is particularly suited for providing original data to be used in lung function diagnostics or in diagnosing lung diseases.

In an embodiment, the marker substance is used in its natural abundance, in a non-radioactive isotopically labelled form (e.g., labelled by $^{13}C$, $^{2}H$ and/or $^{15}N$), or in a mixture of both. The vapor enriched with the marker substance can be generated by a vaporizer, directly from a solution, or by mixing different gases (one with the marker substance).

The enriched vapor can be inhaled via a filled breath bag, an open or closed system with a breath mask connected to the vapor reservoir, or other systems enriching the air with the marker substance vapor.

The marker substance concentration can be measured at any time, namely before inhaling the enriched air, while inhaling the enriched air, directly after inhaling the enriched air, and after inhalation of the enriched air.

Information on the lung properties and the ability for marker substance uptake via the lungs are taken from the measurements before inhaling the enriched air, while inhaling the enriched air, and/or directly after inhaling the enriched air.

Using isotopically labelled marker substances for inhalation allows for separation of naturally occurring marker substance levels and inhalation induced marker substance levels. In case of some marker substances there is a naturally occurring marker substance level in the blood (i.e., a natural abundance), varying for example with the time of the year. Isotopically labelled marker substances can be used to distinguish between the natural occurrence and the induced occurrence of the marker substance in the blood.

In an embodiment, the organ is at least one from the group consisting of liver, kidney, spleen, and lung. Thereby, the liver is particularly suited as organ, the function of which is to be tested. In addition, the lung is also particularly suited as organ, the function which is to be tested. Liver and lung are a particularly suited combination of organs.

In an embodiment, the marker substance is a volatile organic compound (VOC). Such volatile organic compounds are small organic molecules having a comparatively low boiling point. They occur—in different compositions—almost everywhere and are (in comparatively low doses) inhaled and again expired by all organisms. Thereby, a metabolism of these compounds can occur within the subject.

In an embodiment, the marker substance has a vapor pressure above 0.02 mmHg, in particular above 0.03 mmHg, in particular above 0.05 mmHg, in particular above 0.1 mmHg, in particular above 0.2 mmHg, in particular above 0.3 mmHg, in particular above 0.5 mmHg, and especially above 1 mmHg (always at a temperature of 37° C.).

In an embodiment, the marker substance is metabolized by the living organism. Then, the reduction of the marker substance concentration in the exhaled air can be directly related to the metabolization dynamics of the marker substance in the respective organ of the living organism.

The following substances are generally suited as marker substances. They are ordered according to their mass over charge ratio m/z (without $H^+$):

m/z=60: carbonyl sulfide, dimethylsilane, acetic acid, propanol m/z=108: bis(methylthio)methane, 3-mercaptopropane-1,2,-diol m/z=121: cysteine m/z=168: selenocysteine m/z=114: octane, furan-2-ylmethanethiol m/z=80: 1,2-diazine (pyridazine), 1,3-diazine (pyrimidine), 1,4-diazine (pyrazine)

m/z=136: limonene, α-pinene, β-pinene, γ-pinene m/z=86: 2-pentanone, hexane m/z=156: 4-hydroxynonenal m/z=128: nonane, naphthalene Since not all of the before-mentioned marker substances can be equally well inhaled by living organism without causing undesired side effects, the marker substance is, in an embodiment, chosen from the group consisting of octane, furan-2-ylmethanethiol, 1,2-diazine, 1,3-diazine, 1,4-diazine, a terpene, 2-pentanone, hexane and 4-hydroxynonenal. Combinations of these substances are possible.

In an embodiment, the marker substance is at least one diazine, namely 1,2-diazine, 1,3-diazine and/or 1,4-diazine.

In an embodiment, the marker substance is a terpene. In another embodiment, the terpene is chosen from the group consisting of limonene, α-pinene, β-pinene and γ-pinene. Limonene is particularly suited as marker substance.

In an aspect, the invention also relates to a method for determining the function of an organ of a living organism having the features as explained above. Thereby, the method encompasses an additional step of determining the function of the organ based on the concentration difference determined in step d). In an embodiment, the method also comprises the step of reporting the function of the organ. In an embodiment, the method comprises determining the health status of the living organism with respect to and based on the determined organ function. In an embodiment, the method also comprises the step of reporting the health status of the living organism.

In an aspect, the invention also relates to a method for diagnosing a disease or for diagnosing a severity of a disease of an organ of a living organism having the features explained above. Thereby, the method encompasses an additional step of making a diagnosis based on the concentration difference determined in step d).

In an aspect, the invention also relates to the use of at least one substance chosen from the group consisting of octane, furan-2-ylmethanethiol, 1,2-diazine, 1,3-diazine, 1,4-diazine, a terpene, 2-pentanone, hexane and 4-hydroxynonenal as marker substance to be administered to a living organism by inhalation in a method for providing original data that can be used for subsequently determining the function of an organ of the living organism or for subsequently diagnosing a disease or a severity of a disease of an organ of the living organism.

In an embodiment, the terpene is at least one of the group consisting of limonene, α-pinene, β-pinene and γ-pinene.

In an aspect, the invention also relates to the further medical use of a substance chosen from the group consisting of octane, furan-2-ylmethanethiol, 1,2-diazine, 1,3-diazine, 1,4-diazine, a terpene, 2-pentanone, hexane and 4-hydroxynonenal, namely for use as marker substance to be administered to a living organism by inhalation in a diagnostic method for determining the function of an organ of the living organism or for diagnosing a disease or a severity of a disease of an organ of the living organism.

In an embodiment, the terpene is at least one of the group consisting of limonene, α-pinene, β-pinene and γ-pinene.

All embodiments explained with respect to the described methods, uses and further medical uses can be combined in any desired way. Thereby, embodiments of the described methods can be transferred to the respective other method, described use and further medical use of the marker substances and vice versa.

BRIEF DESCRIPTION OF THE DRAWINGS

Aspects of the instant invention will now be explained with respect to exemplary embodiments and accompanying Figures.

DETAILED DESCRIPTION

Exemplary Embodiments

Suited marker substances were identified by re-evaluating the experimental data of the dissertation "Analysis of breath allows for non-invasive identification and quantification of diseases and metabolic dysfunction" of Suha Adel Al-Ani that is freely available under the following internet address: www.diss.fu-berlin.de/diss/receive/FUDISS_thesis_000000100227

Further details of the concrete experimental work that has been done to obtain the data explained in the following can be found in chapter 4 of this dissertation. This dissertation, in particular chapter 4 regarding the experimental work, chapter 3 regarding details of DOB kinetics, and the graphically depicted results of chapter 5, is hereby incorporated by reference.

Briefly, the exhaled breath of healthy individuals belonging to two groups of different nutritional states (namely based on a normal diet on the one hand and based on a vegan diet on the other hand) as well as of patients suffering from a liver disease has been measured by proton-transfer reaction mass spectrometry (PTR-MS) for quantitatively identifying different volatile organic compounds (VOCs) in the measured exhaled breath.

Figure 1A:
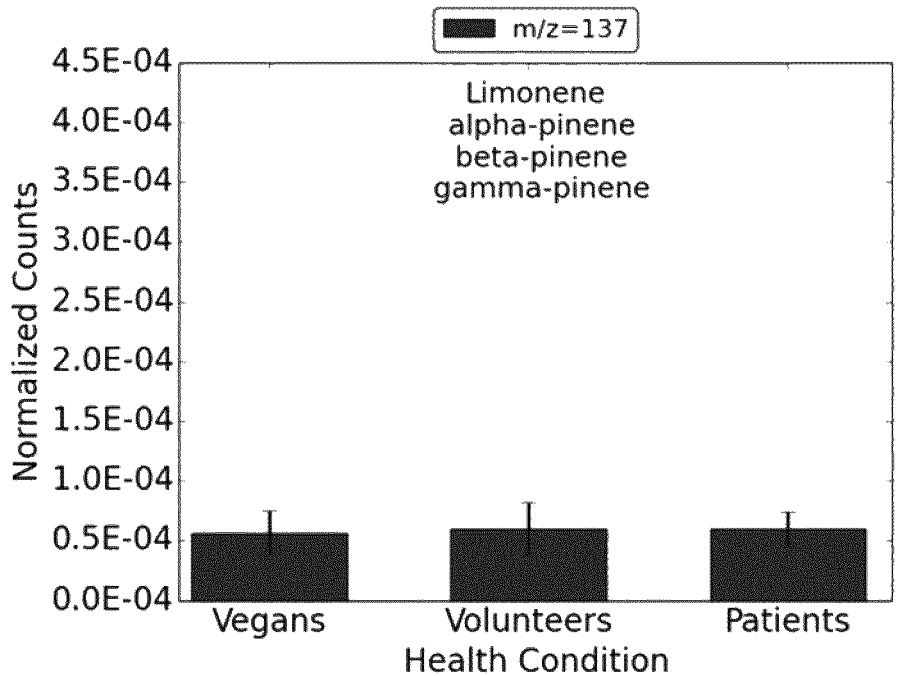
FIG. 1A shows the results of proton-transfer reaction mass spectrometry (PTR-MS) with respect to compounds having an m/z value of 137 of exhaled breath of individuals having divers health conditions or nutritional states.

FIG. 1A shows the results of according PTR-MS measurements regarding limonene and different pinenes as marker substances that are typically inhaled from the surrounding to identify liver diseases or impaired liver function. The concentration of limonene, α-pinene, β-pinene and γ-pinene (all having an m/z ratio of 137 including an additional H$^+$; their mass without a proton is 136 au) is almost identical for all three groups of individuals tested (taking into account the error bars).

In addition, the liver power of the same individuals was tested by determining the LiMAx value on the basis of a breath test after $^{13}$C-methacetin administration. Thereby, the LiMAx value was calculated according to the following formula:

$$LiMAx = \frac{DOB_{max} \cdot R_{PDB} \cdot P_{CO_2} \cdot M}{BW},$$

wherein the unit of the LiMAx value is (m/kg)/h, $DOB_{max}$ denotes the maximum value of the DOB (delta over baseline) kinetics, $R_{PDB}$ is the Pee Dee Belemnite standard and is 0.011237, $P_{CO2}$ denotes the CO$_2$ production rate that is to be calculated by (300 mmol/h)*BSA, wherein BSA means body surface area; it is indicated in m$^2$ and is calculated according to the Du Bois formula: BSA=0.007184*W$^{0.425}$*H$^{0.725}$, wherein W is the weight in kg and H is the height in cm of the respective individual;

M is the molar mass of $^{13}$C-methacetin (166.19 g/mol),

BW is the body weight of the individual in kg.

Figure 1B:
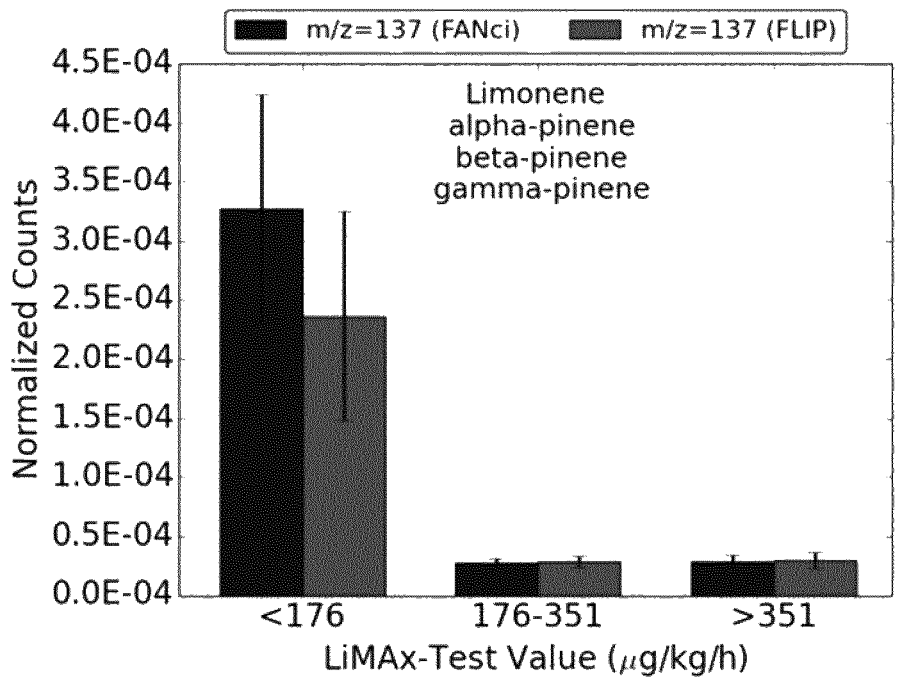
FIG. 1B shows the results of PTR-MS of exhaled breath with respect to compounds having an m/z value of 137 of exhaled breath of the same individuals as in FIG. 1A in dependence on the liver power (expressed as LiMAx value) that has been determined for these individuals independently on the PTR-MS measurement.

FIG. 1B shows the results of PTR-MS measurements in dependence on an according determination of the LiMAx value. It can be seen from FIG. 1B that the concentration of limonene, α-pinene, β-pinene and γ-pinene is significantly increased in the expiratory air of patients that have a strongly impaired liver function represented by a LiMAx value of below 176 (both bars on the left) as compared to patients with only slightly impaired liver function represented by a LiMAx value of 176 to 351 (both bars in the middle) or individuals with normal liver function represented by a LiMAx value of above 351 (both bars on the right) that were erroneously grouped as patients suffering from a liver disease but that have in fact no decreased liver function. Thereby, the LiMAx value has been determined by two independent devices, namely by a modified non-dispersive isotope-selective infrared spectrometer of Fischer Analysen Instrumente GmbH (black bars, abbreviated by FANci or FANci2-db16) or by a Flow-through Fast Liver Investigation Packet available from Humedics GmbH (grey bars, abbreviated by FLIP).

The modified non-dispersive isotope-selective infrared spectrometer FANci2-db16 has a frequency of approximately 1/min. It was used to draw and analyze breath samples. This spectrometer measures the $^{13}$CO$_2$ to $^{12}$CO$_2$ ratio. As a light source, a black body radiator is used. Two detection chambers are filled with $^{13}$CO$_2$ or $^{12}$CO$_2$, respectively, wherein a microphone is present in each detection chamber. Between the light source and the detection chamber there is a chopper to modulate the IR radiation. A measuring chamber is filled with the gas to be tested. The molecules in the detection chambers absorb the modulated IR radiation and convert it to thermal energy. The so-modulated density fluctuations cause sound waves, and each is measured with a microphone.

The disadvantage of the device is that it is very sensitive to vibrations and to temperature changes. Also, the breath cannot be measured when flowing so that it is instead kept stationary in an aluminum bag. In standard mode, the breath is collected in a bag and the bag is connected to the device, then it pumps the exhaled air into the measuring chamber. During exhaling air in to the bag, it is important to make sure that only the alveolar air is used. The air that does not reach the alveoli has the CO$_2$ content of the inspired air. It would distort the measured values. With this measuring method an accuracy of ±2 DOB can be achieved according to the manufacturer, but it does not provide absolute values for exhaled CO$_2$ volumes.

The FLIP device can measure the $^{13}$CO$_2$ to $^{12}$CO$_2$ ratio in exhaled breath. The ultra-sensitive laser spectroscopy system of the FLIP device can quickly and reliably determine the capacity of the liver function. The FLIP/LiMAx system greatly improves the surgical intervention planning. The laser based FLIP device detects a metabolic product ($^{13}$CO$_2$) of the enzymatic conversion of the drug methacetin in the liver in the exhaled air. $^{13}CO_2$ is stable, non-radioactive and detected by the unique sensors in the device even at extremely low concentrations (100 ppb) in every single breath.

The FLIP device measures in real-time a continuous flow of air. It has been developed in cooperation with medical professionals and is adapted to various clinical situations. The FLIP has unified the mobility, the usability and the practicality. It has been used successfully in various intensive care units, emergency rooms, operating theatres and outpatient stations.

The data shown in FIGS. 1A and 1B was interpreted in the above-mentioned dissertation such that the according substances were held to be no good biomarkers, since the amount of inhaled marker substance was typically not known, and thus the reference was missing.

However, it turned out that this statement is a misinterpretation of the data. In contrast to this statement, limonene is a well suited marker substance within the context of aspects of the present invention. Limonene has a low vapor pressure and a pleasant odor.

After inhalation of air with marker substance vapor (marker substance gas) the exhaled marker substance concentration is measured. This provides useful information on the lung status, when the concentration of the marker substance gas is known, because this provides direct information on the exchange rate of the lung.

After some time after the inhalation, the concentration of the marker substance in the exhaled air is measured again. A reduction in concentration (in particular the course of concentration over time) of the marker substance directly reflects the metabolization of the marker substance and thus its decomposition within the living organism.

The marker substances referred to in FIGS. 1A and 1B are clearly decomposed slower in patients with impaired liver function. It was reported that limonene is metabolized by enzymes of the Cytochrome P450 family. [Mizayawa, M. et al. The American Society for Pharmacology and Experimental Therapeutics, Vol. 30, No. 5, (2002), 602-607] Thus, the higher concentration of the marker substance in the exhaled air in case of patients suffering from liver disease provides direct qualitative or quantitative information on the impaired liver function. Hence, measurement of exhaled marker substance concentration provides a fast test for severe liver diseases or impaired liver function.

Mizayawa et al. also reported that limonene is known to have chemopreventive activity, and is metabolized in human liver cells by CYP 2C9 and CYP 2C19 to carveol and perillyl alcohol. Other enzymes like CYP 2C8, 2C18, and 3A4 could also play a role in this metabolization. Michael N. Gold reported in Environmental Health Perspectives, Vol. 105, Supplement 4, 1997, pages 977-979 that "Monoterpenes such as limonene and perillyl alcohol have been shown to prevent mammary, liver, lung, and other cancers".

The use of limonene as marker substances to detect liver diseases or an impaired liver function is thus connected with the additional effect of preventing mammary, liver, lung and other cancers. Moreover, the liver metabolization product of limonene, perillyl alcohol, also prevents liver and other cancers.

In summary, by using limonene as marker substance, a natural product is used as marker substance to detect liver diseases or an impaired liver function. Limonene itself has a preventive influence on liver and other cancers. Moreover, limonene can be easily inhaled, thus allowing its use in a purely non-invasive method. Limonene is also comfortable for the patients, because of its pleasant odor. Furthermore, it provides direct information on the lung function by detecting the blood concentration change upon inhalation of the marker substance.

In contrast to prior art methods, in this exemplary embodiment limonene is administered as marker substance by inhalation. Afterwards, its metabolization via enzymes of the Cytochrome P450 enzyme family is followed by detecting the level of the administered marker substance in the exhaled air (not of the metabolized product).

Besides limonene and/or the pinenes referred to in the first exemplary embodiment, other marker substances can be used for the described methods. These marker substances are generally characterized by two properties that need to be fulfilled. First property: Comparison of the marker substance concentrations of the three groups of vegan persons, volunteers, and patients (cf. FIG. 1A) shows no significant difference (within the error bars, i.e. taking the error bars into account). Second property: Comparison of the marker substance concentrations of three different liver function groups represented by three different ranges of the LiMAx value (cf. FIG. 1B) shows differences (within the error bars, i.e. taking the error bars into account).

By applying these criteria to experimental data that has been previously obtained and already analyzed under a different point of view, more suited marker substances for determining the function of an organ of a living organism or for subsequently diagnosing a disease or a severity of a disease of an organ of a living organism were identified. The according data is shown in FIGS. 2A to 10B.

Thereby, all FIGS. indicate the m/z ratio of the substances identified in exhaled breath by considering an additional proton applied to the substances during PTR-MS for ionization purposes.

The results shown in FIGS. 2A, 3A, 4A, 5A, 6A, 7A, 8A, 9A, and 10A has been obtained in the same way as in case of FIG. 1A. The results shown in FIGS. 2B, 3B, 4B, 5B, 6B, 7B, 8B, 9B, and 10B has been obtained in the same way as in case of FIG. 1B.

Figure 2A:
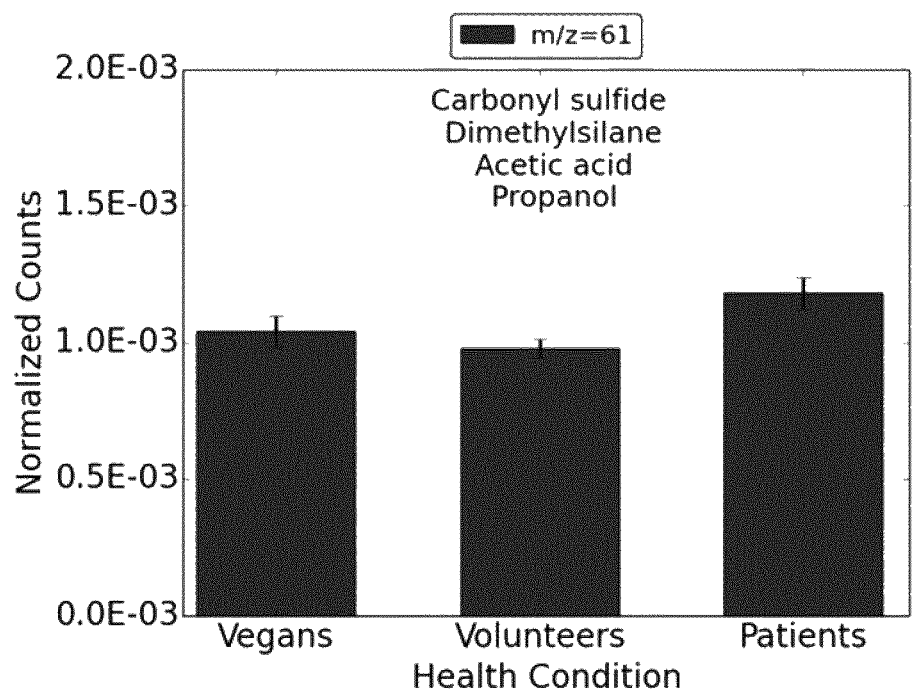
FIG. 2A shows the results of proton-transfer reaction mass spectrometry (PTR-MS) with respect to compounds having an m/z value of 61 of exhaled breath of individuals having divers health conditions or nutritional states.
Figure 2B:
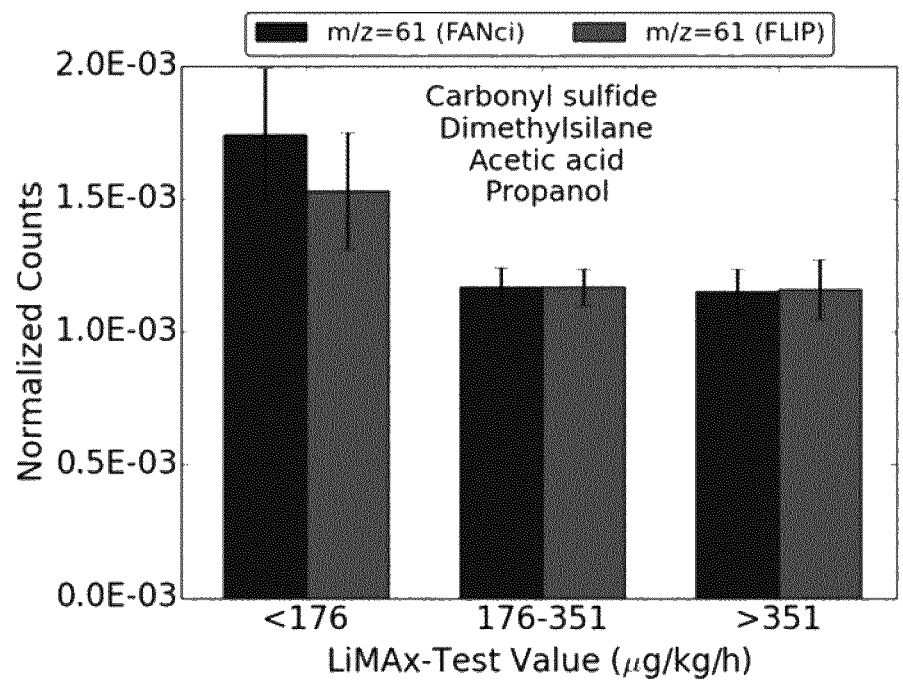
FIG. 2B shows the results of PTR-MS of exhaled breath with respect to compounds having an m/z value of 61 of exhaled breath of the same individuals as in FIG. 2A in dependence on the liver power (expressed as LiMAx value) that has been determined for these individuals independently on the PTR-MS measurement.

FIGS. 2A and 2B indicate that carbonyl sulfide, dimethylsilane, acetic acid and/or propanol (having an m/z ratio of 61) are suited markers for determining the function of an organ of a living organism or for subsequently diagnosing a disease or a severity of a disease of an organ of a living organism.

Figure 3A:
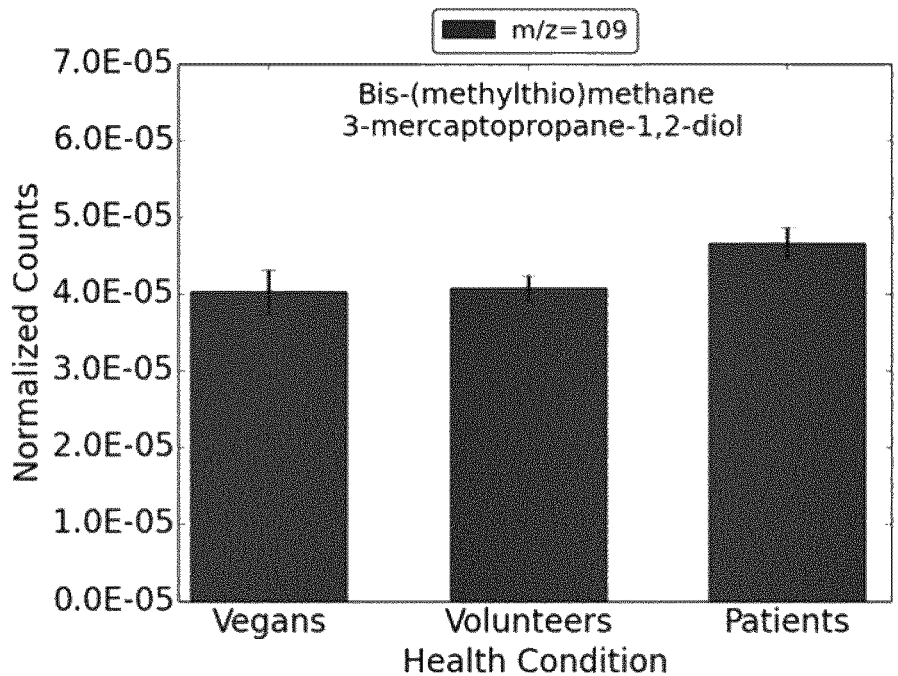
FIG. 3A shows the results of proton-transfer reaction mass spectrometry (PTR-MS) with respect to compounds having an m/z value of 109 of exhaled breath of individuals having divers health conditions or nutritional states.
Figure 3B:
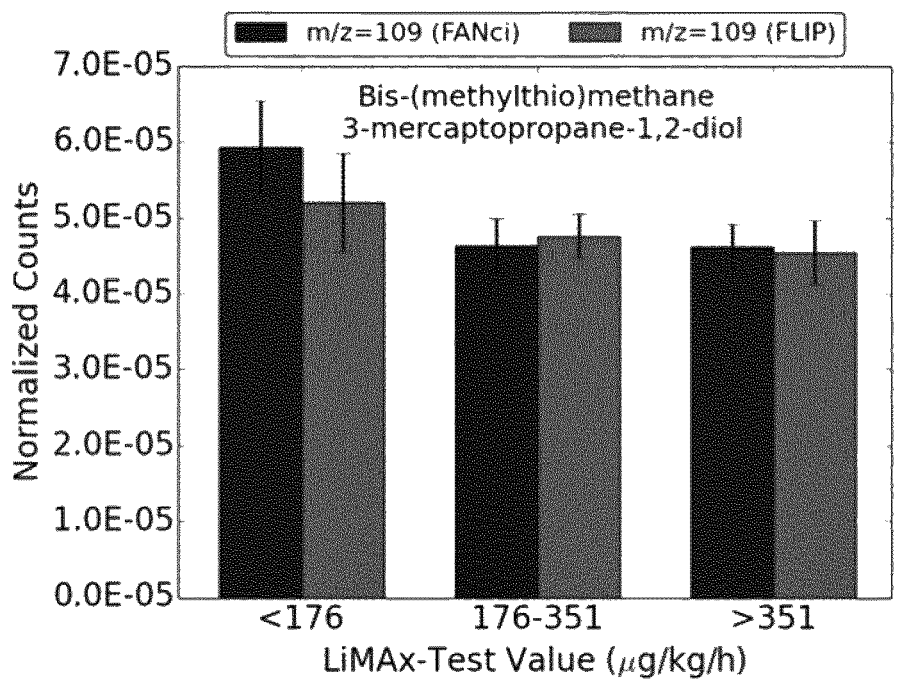
FIG. 3B shows the results of PTR-MS of exhaled breath with respect to compounds having an m/z value of 109 of exhaled breath of the same individuals as in FIG. 3A in dependence on the liver power (expressed as LiMAx value) that has been determined for these individuals independently on the PTR-MS measurement.

FIGS. 3A and 3B indicate that bis(methylthio)methane and/or 3-mercaptopropane-1,2,-diol (having an m/z ratio of 109) are suited markers for determining the function of an organ of a living organism or for subsequently diagnosing a disease or a severity of a disease of an organ of a living organism.

Figure 4A:
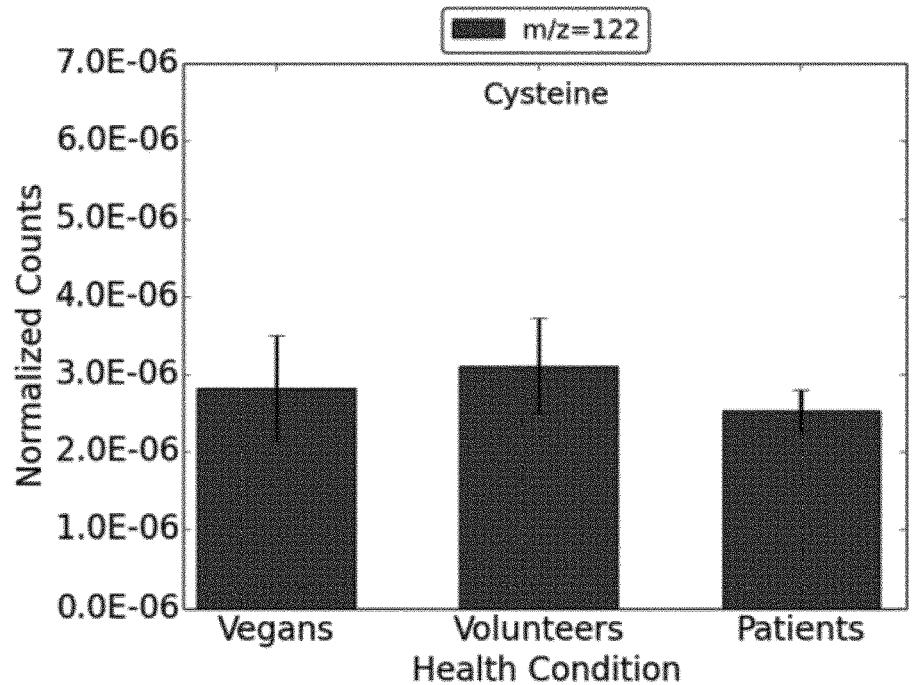
FIG. 4A shows the results of proton-transfer reaction mass spectrometry (PTR-MS) with respect to cysteine having an m/z value of 122 of exhaled breath of individuals having divers health conditions or nutritional states.
Figure 4B:
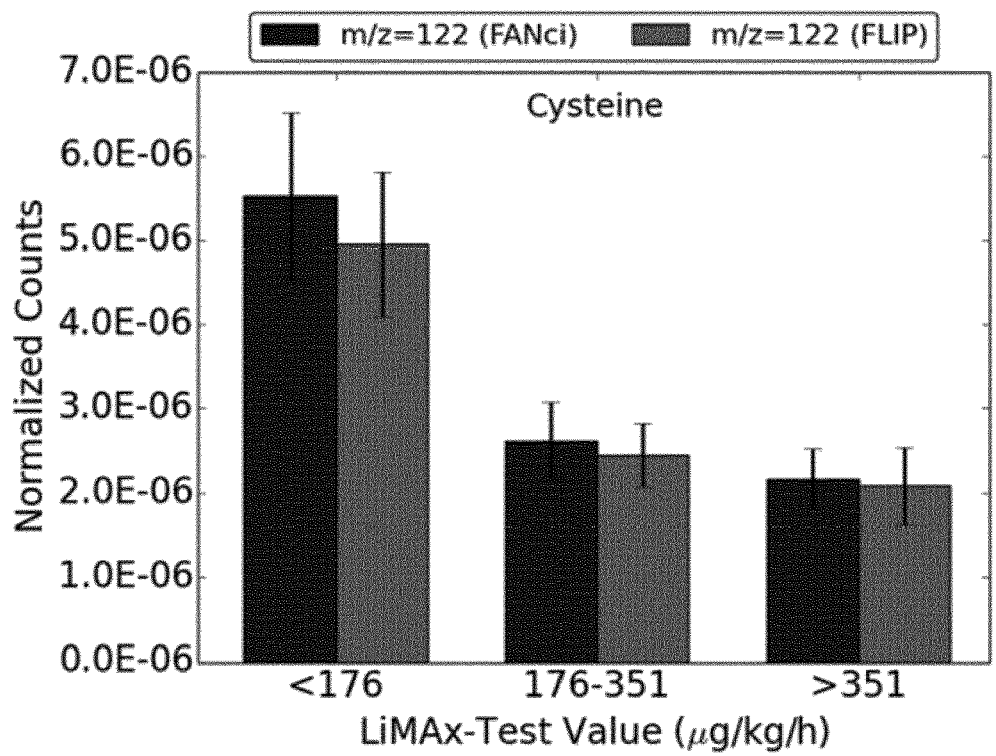
FIG. 4B shows the results of PTR-MS of exhaled breath with respect to cysteine having an m/z value of 122 of exhaled breath of the same individuals as in FIG. 4A in dependence on the liver power (expressed as LiMAx value) that has been determined for these individuals independently on the PTR-MS measurement.

FIGS. 4A and 4B indicate that cysteine (having an m/z ratio of 122) is a suited marker for determining the function of an organ of a living organism or for subsequently diagnosing a disease or a severity of a disease of an organ of a living organism.

Figure 5A:
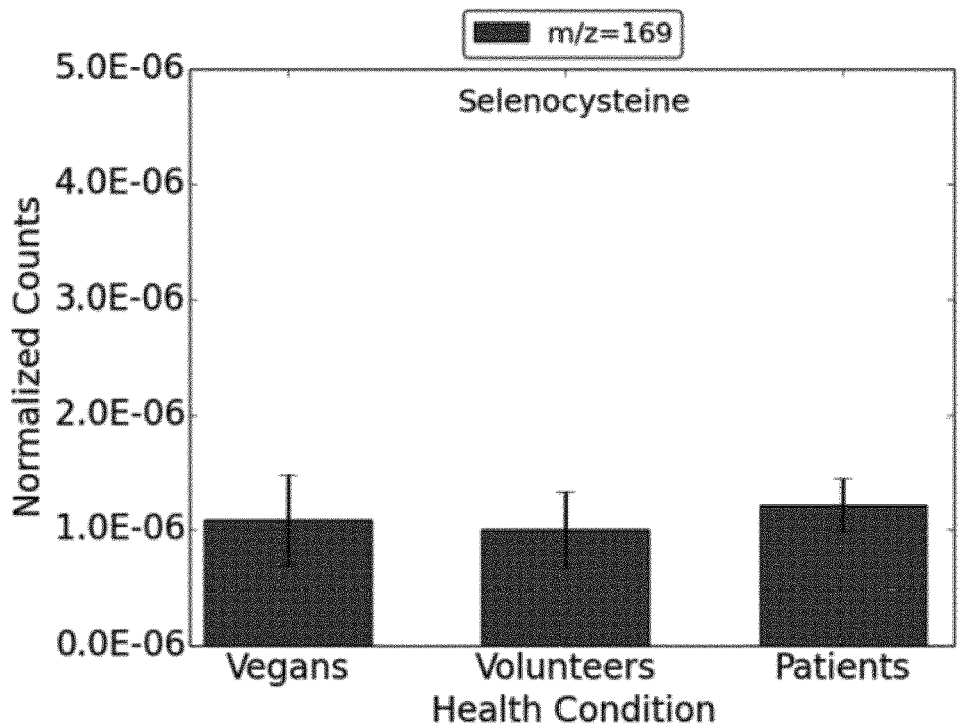
FIG. 5A shows the results of proton-transfer reaction mass spectrometry (PTR-MS) with respect to selenocysteine having an m/z value of 169 of exhaled breath of individuals having divers health conditions or nutritional states.
Figure 5B:
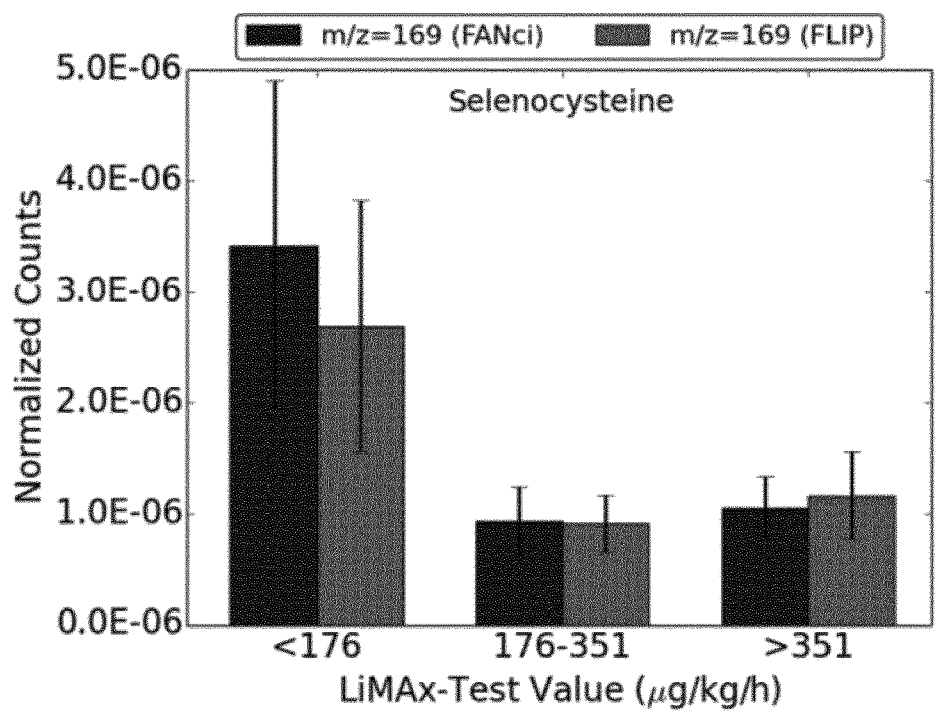
FIG. 5B shows the results of PTR-MS of exhaled breath with respect to selenocysteine having an m/z value of 169 of exhaled breath of the same individuals as in FIG. 5A in dependence on the liver power (expressed as LiMAx value) that has been determined for these individuals independently on the PTR-MS measurement.

FIGS. 5A and 5B indicate that selenocysteine (having an m/z ratio of 169) is a suited marker for determining the function of an organ of a living organism or for subsequently diagnosing a disease or a severity of a disease of an organ of a living organism.

Figure 6A:
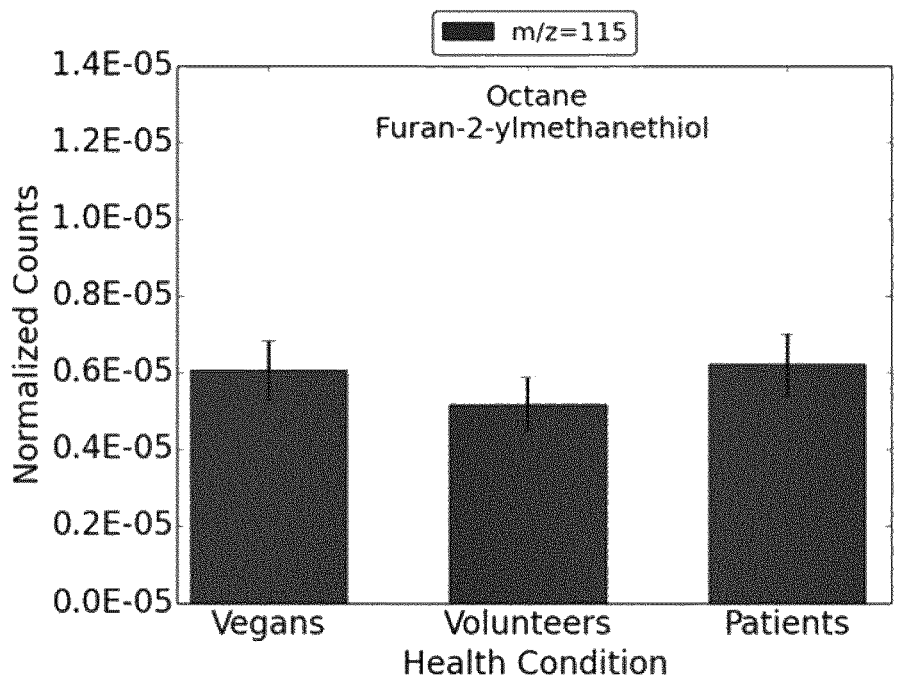
FIG. 6A shows the results of proton-transfer reaction mass spectrometry (PTR-MS) with respect to compounds having an m/z value of 115 of exhaled breath of individuals having divers health conditions or nutritional states.
Figure 6B:
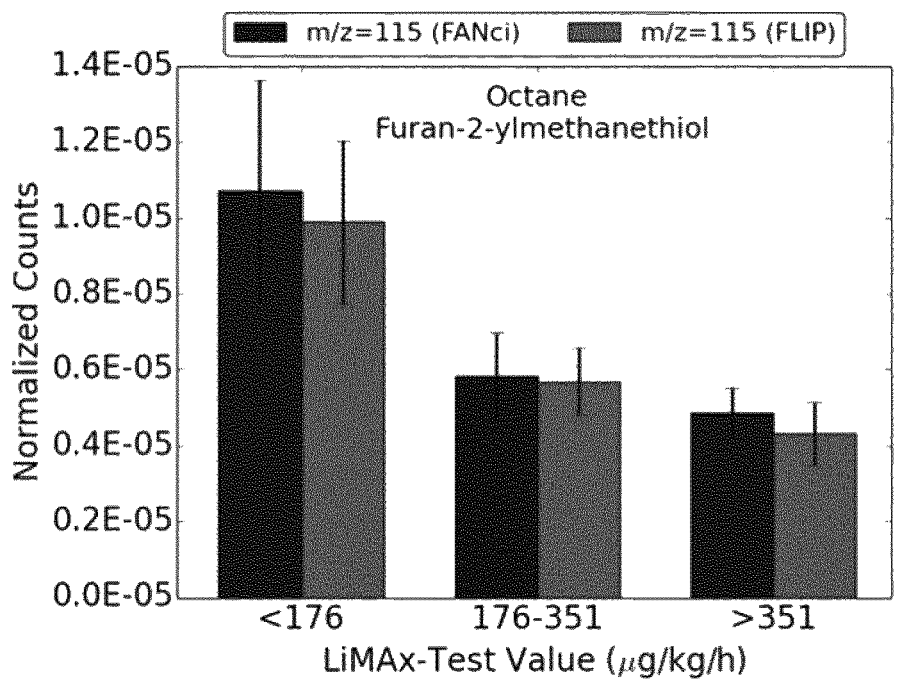
FIG. 6B shows the results of PTR-MS of exhaled breath with respect to compounds having an m/z value of 115 of exhaled breath of the same individuals as in FIG. 6A in dependence on the liver power (expressed as LiMAx value) that has been determined for these individuals independently on the PTR-MS measurement.

FIGS. 6A and 6B indicate that octane and/or furan-2-ylmethanethiol (having an m/z ratio of 115) are suited markers for determining the function of an organ of a living organism or for subsequently diagnosing a disease or a severity of a disease of an organ of a living organism.

Figure 7A:
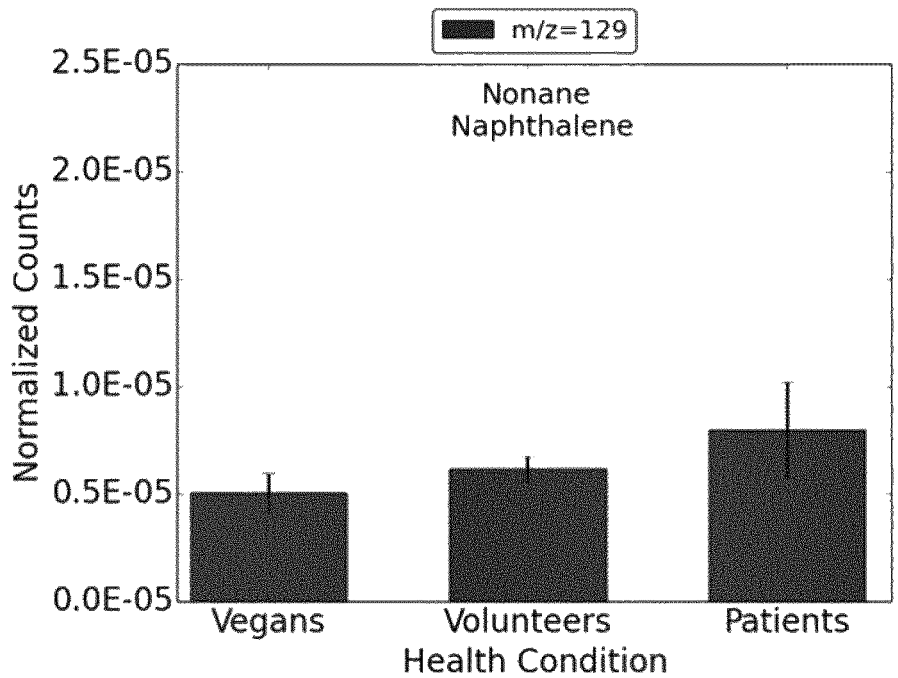
FIG. 7A shows the results of proton-transfer reaction mass spectrometry (PTR-MS) with respect to compounds having an m/z value of 129 of exhaled breath of individuals having divers health conditions or nutritional states.
Figure 7B:
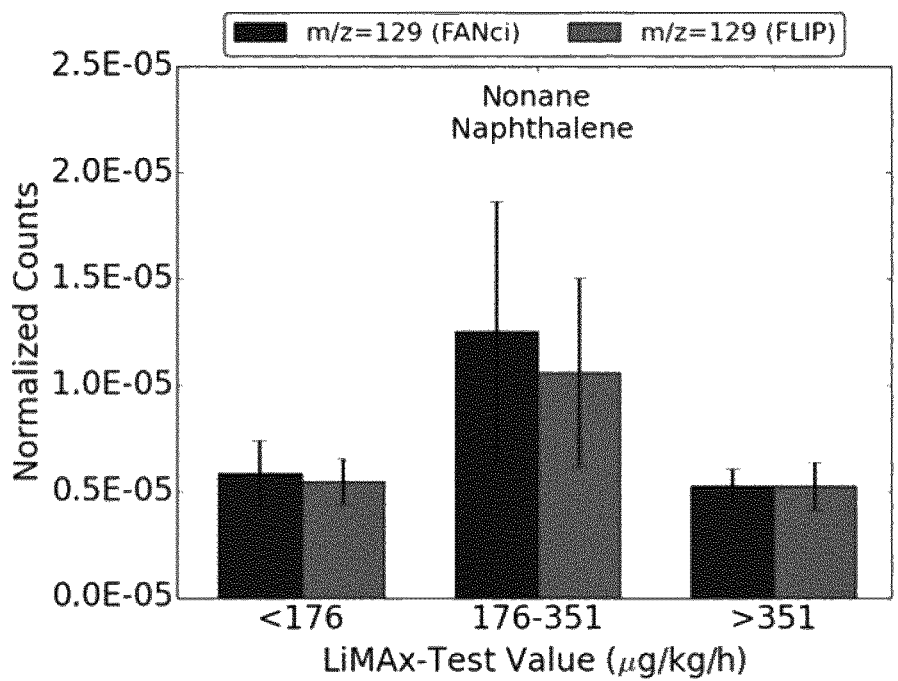
FIG. 7B shows the results of PTR-MS of exhaled breath with respect to compounds having an m/z value of 129 of exhaled breath of the same individuals as in FIG. 7A in dependence on the liver power (expressed as LiMAx value) that has been determined for these individuals independently on the PTR-MS measurement.

FIGS. 7A and 7B indicate that nonane and/or naphthalene (having an m/z ratio of 129) are suited markers for determining the function of an organ of a living organism or for subsequently diagnosing a disease or a severity of a disease of an organ of a living organism.

Figure 8A:
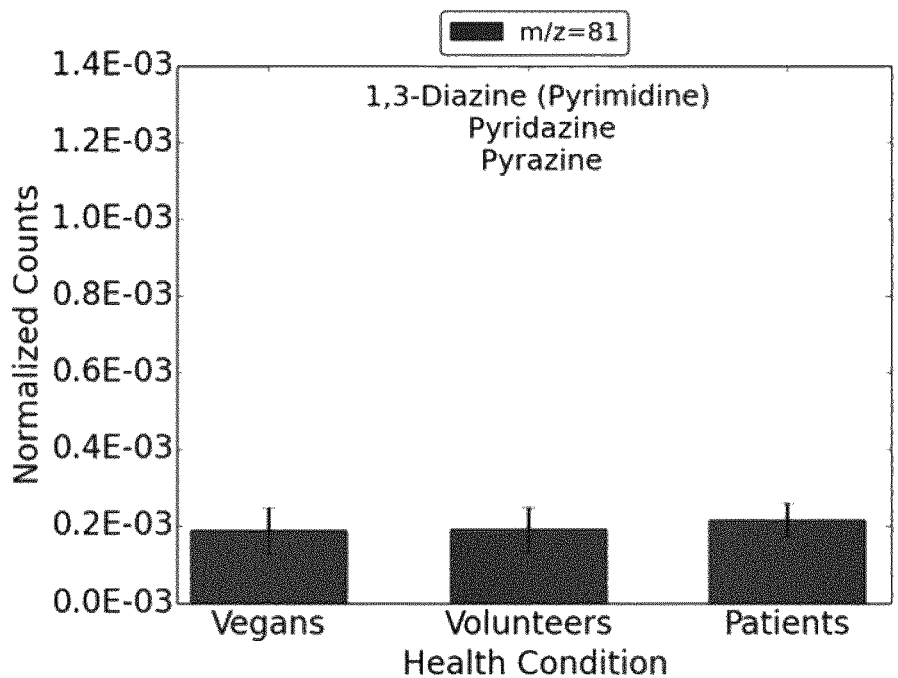
FIG. 8A shows the results of proton-transfer reaction mass spectrometry (PTR-MS) with respect to compounds having an m/z value of 81 of exhaled breath of individuals having divers health conditions or nutritional states.
Figure 8B:
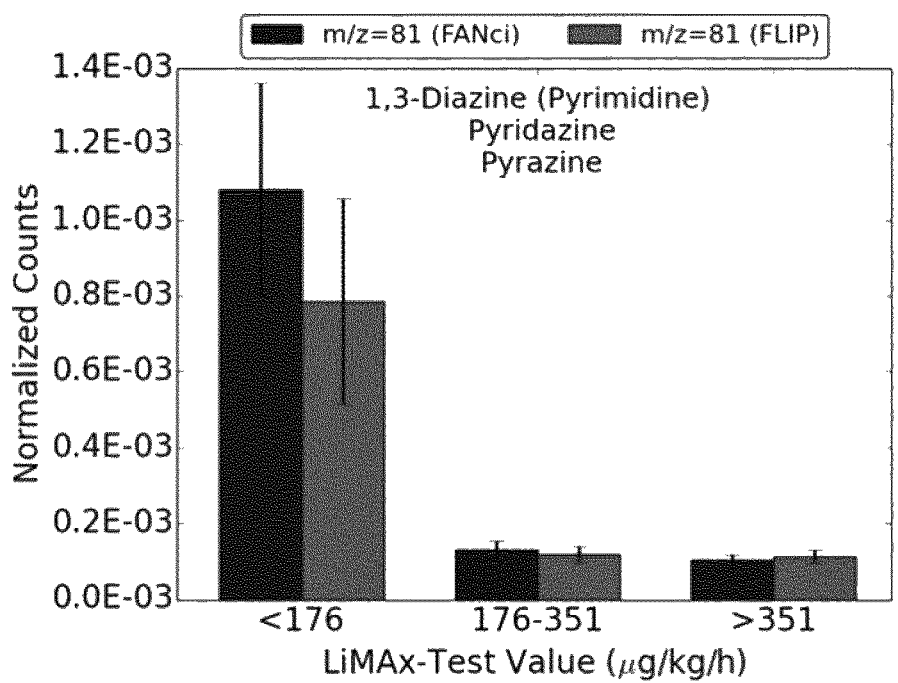
FIG. 8B shows the results of PTR-MS of exhaled breath with respect to compounds having an m/z value of 81 of exhaled breath of the same individuals as in FIG. 8A in dependence on the liver power (expressed as LiMAx value) that has been determined for these individuals independently on the PTR-MS measurement.

FIGS. 8A and 8B indicate that 1,2-diazine (pyridazine), 1,3-diazine (pyrimidine) and/or 1,4-diazine (pyrazine) (having an m/z ratio of 81) are suited markers for determining the function of an organ of a living organism or for subsequently diagnosing a disease or a severity of a disease of an organ of a living organism.

Figure 9A:
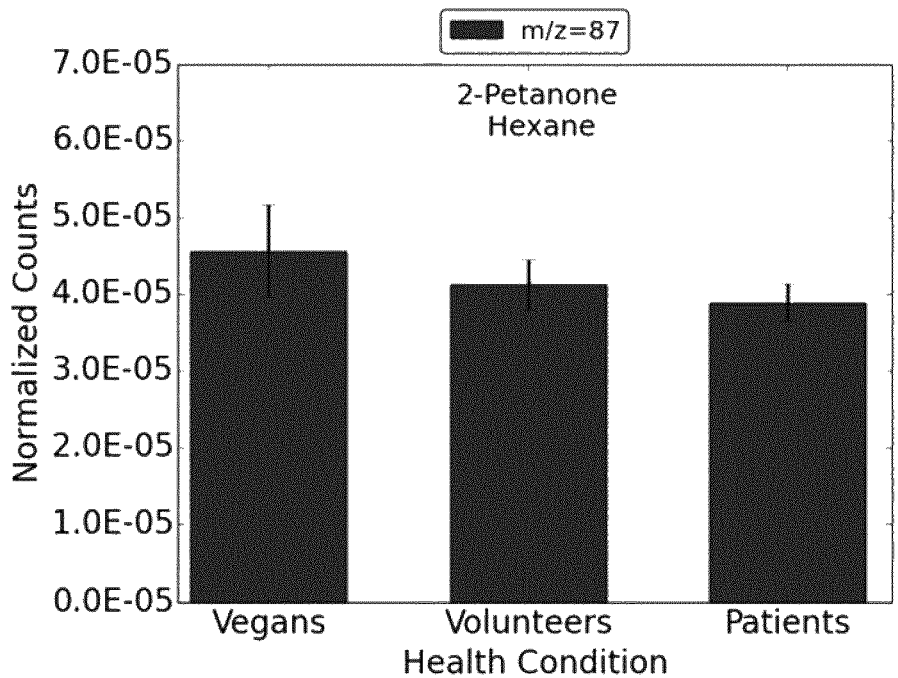
FIG. 9A shows the results of proton-transfer reaction mass spectrometry (PTR-MS) with respect to compounds having an m/z value of 87 of exhaled breath of individuals having divers health conditions or nutritional states.
Figure 9B:
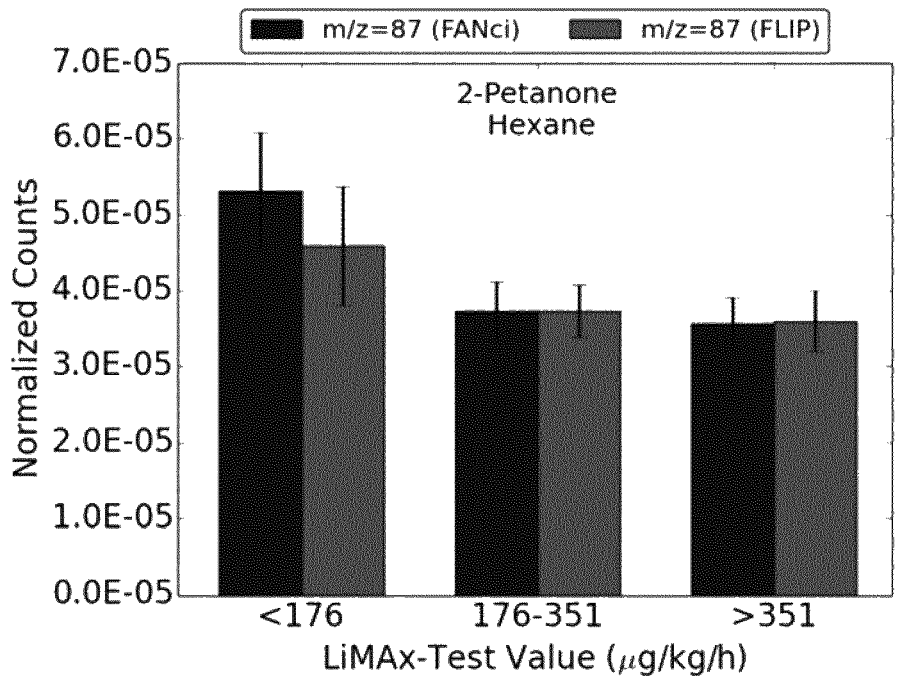
FIG. 9B shows the results of PTR-MS of exhaled breath with respect to compounds having an m/z value of 87 of exhaled breath of the same individuals as in FIG. 9A in dependence on the liver power (expressed as LiMAx value) that has been determined for these individuals independently on the PTR-MS measurement.

FIGS. 9A and 9B indicate that 2-pentanone and/or hexane (having an m/z ratio of 87) are suited markers for determining the function of an organ of a living organism or for subsequently diagnosing a disease or a severity of a disease of an organ of a living organism.

Figure 10A:
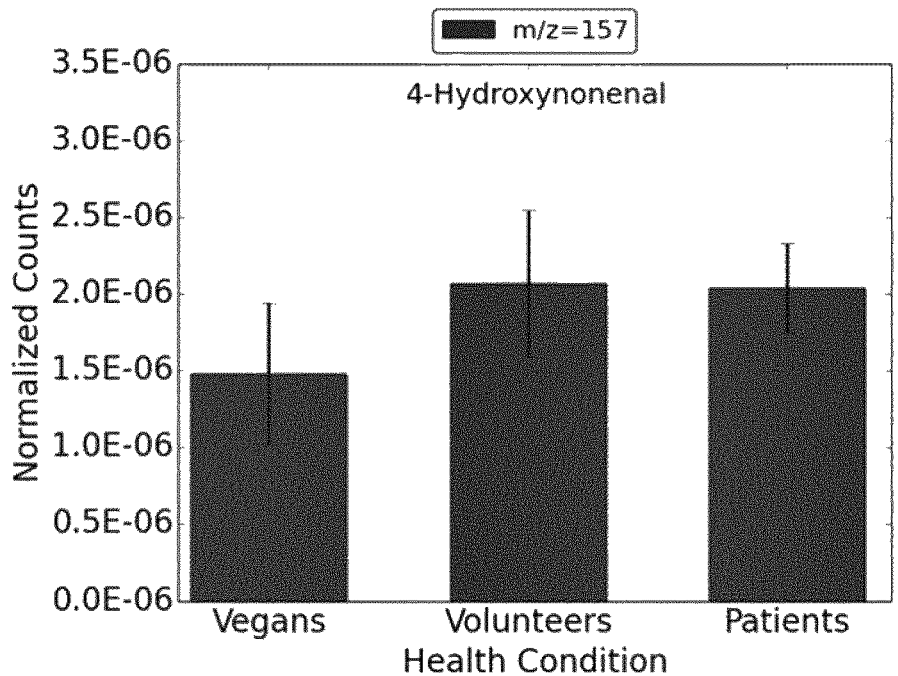
FIG. 10A shows the results of proton-transfer reaction mass spectrometry (PTR-MS) with respect to 4-hydroxynonenal having an m/z value of 157 of exhaled breath of individuals having divers health conditions or nutritional states.
Figure 10B:
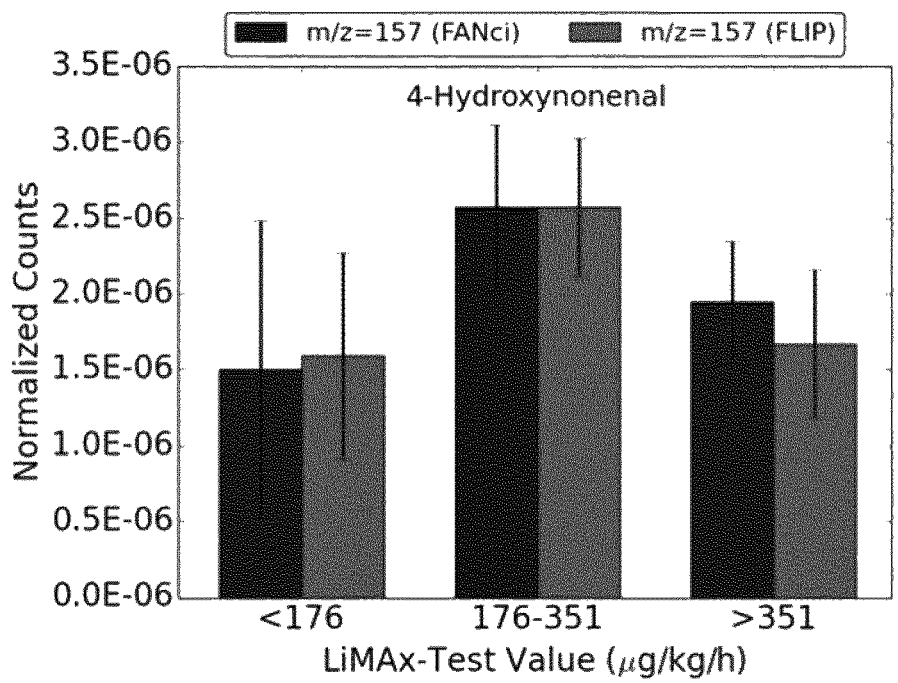
FIG. 10B shows the results of PTR-MS of exhaled breath with respect to 4-hydroxynonenal having an m/z value of 157 of exhaled breath of the same individuals as in FIG. 10A in dependence on the liver power (expressed as LiMAx value) that has been determined for these individuals independently on the PTR-MS measurement.

FIGS. 10A and 10B indicate that 4-hydroxynonenal (having an m/z ratio of 157) is a suited marker for determining the function of an organ of a living organism or for subsequently diagnosing a disease or a severity of a disease of an organ of a living organism.

What claimed is:

1. A method for determining the liver function of a human patient, the method comprising the following steps:
    a) administering a volatile organic compound to a human patient by inhalation, wherein the volatile organic compound has a vapor pressure above 0.01 mmHg at 37° C., wherein the volatile organic compound is at least one substance chosen from the group consisting of octane, furan-2-ylmethanethiol, 1,2-diazine, 1,3-diazine, 1,4-diazine, a terpene, 2-pentanone, hexane and 4-hydroxynonenal,
    b) collecting exhaled air from the human patient,
    c) determining a concentration of the volatile organic compound in exhaled air which is exhaled by the human patient at a first time point, wherein the first time point is a time point after inhalation of the volatile organic compound,
    d) determining the concentration of the volatile organic compound in the exhaled air which is exhaled by the human patient at a plurality of further time points after the first time point, so as to obtain a plurality of data points relating to the concentration of the volatile organic compound at different time points, wherein a difference between the first time point and the latest of the further time points lies in a range of 30 seconds to 70 minutes,
    e) determining a time-resolved metabolization dynamics of the volatile organic compound on the basis of differences between the concentration of the volatile organic compound determined at the first time point and the concentration of the volatile organic compound determined at each of the further time points, and
    f) determining the liver function based on the time-resolved metabolization dynamics determined in step d).

2. The method of claim 1, wherein the method also comprises the step of reporting the liver function.

3. The method of claim 1, wherein the method comprises determining the health status of the human patient with respect to and based on the determined liver function.

4. The method of claim 3, wherein the method also comprises the step of reporting the health status of the human patient.

5. The method of claim 1, wherein the terpene is at least one of the group consisting of limonene, α-pinene, β-pinene and γ-pinene.

6. A method for diagnosing a disease or for diagnosing a severity of a disease of the liver of a human patient, the method comprising the following steps:
    a) administering a volatile organic compound to a human patient by inhalation, wherein the volatile organic compound has a vapor pressure above 0.01 mmHg at 37° C., wherein the volatile organic compound is at least one substance chosen from the group consisting of octane, furan-2-ylmethanethiol, 1,2-diazine, 1,3-diazine, 1,4-diazine, a terpene, 2-pentanone, hexane and 4-hydroxynonenal,
    b) collecting exhaled air from the human patient,
    c) determining a concentration of the volatile organic compound in exhaled air which is exhaled by the human patient at a first time point, wherein the first time point is a time point after inhalation of the volatile organic compound,
    b) determining the concentration of the volatile organic compound in the exhaled air which is exhaled by the human patient at a plurality of further time points after the first time point, so as to obtain a plurality of data points relating to the concentration of the volatile organic compound at different time points, wherein a difference between the first time point and the latest of the further time points lies in a range of 30 seconds to 70 minutes,
    e) determining a time-resolved metabolization dynamics of the volatile organic compound on the basis of differences between the concentration of the volatile organic compound determined at the first time point and the concentration of the volatile organic compound determined at each of the further time points, and
    f) making a diagnosis based on the time-resolved metabolization dynamics determined in step d).

7. The method of claim 6, wherein the terpene is at least one of the group consisting of limonene, α-pinene, β-pinene and γ-pinene.

* * * * *